US007799535B1

(12) United States Patent
Lindquist

(10) Patent No.: US 7,799,535 B1
(45) Date of Patent: Sep. 21, 2010

(54) METHODS FOR IDENTIFYING FACTORS THAT CONTROL THE FOLDING OF AMYLOID PROTEINS OF DIVERSE ORIGIN

(75) Inventor: Susan Lindquist, Chicago, IL (US)

(73) Assignee: ARCH Development Corporation, Chicago, IL (US)

(*) Notice: Subject to any disclaimer, the term of this patent is extended or adjusted under 35 U.S.C. 154(b) by 117 days.

(21) Appl. No.: 09/207,649

(22) Filed: Dec. 8, 1998

Related U.S. Application Data

(60) Provisional application No. 60/069,168, filed on Dec. 9, 1997, provisional application No. 60/084,824, filed on May 8, 1998.

(51) Int. Cl.
*G01N 33/53* (2006.01)
*G01N 33/569* (2006.01)
*G01N 33/567* (2006.01)
*C12Q 1/00* (2006.01)

(52) U.S. Cl. ............... 435/7.31; 435/4; 435/7.1; 435/7.2; 435/7.21; 435/7.8; 436/501

(58) Field of Classification Search ............... 435/254.2, 435/255.2, 471; 530/325, 326, 300, 371, 530/839
See application file for complete search history.

(56) References Cited

U.S. PATENT DOCUMENTS

| | | | |
|---|---|---|---|
| 5,492,812 A | 2/1996 | Voohies | |
| 5,547,841 A | 8/1996 | Marotta et al. ............... | 435/6 |
| 5,643,562 A | 7/1997 | Kisilevsky et al. | |
| 5,652,092 A | 7/1997 | Vitek et al. ............... | 435/4 |
| 5,686,288 A | 11/1997 | MacDonald et al. | |
| 5,693,757 A | 12/1997 | MacDonald et al. | |
| 5,854,204 A * | 12/1998 | Findeis et al. | |
| 5,952,217 A | 9/1999 | Gorman et al. | |
| 5,958,721 A | 9/1999 | Marshall et al. | |
| 5,994,084 A | 11/1999 | Anderton et al. | |
| 6,071,694 A | 6/2000 | Takashima et al. | |
| 6,093,549 A | 7/2000 | Ross et al. | |
| 7,045,290 B2 | 3/2006 | Lindquist et al. | |
| 2001/0006793 A1 | 7/2001 | Bjornsti et al. | |
| 2002/0187157 A1 | 12/2002 | Jensen et al. | |
| 2003/0022243 A1 | 1/2003 | Kondejewski et al. | |
| 2003/0073610 A1 | 4/2003 | Lindquist et al. | |
| 2005/0009019 A1 | 1/2005 | Van Lueven et al. | |
| 2005/0064548 A1 | 3/2005 | Lindquist et al. | |
| 2006/0141449 A1 | 6/2006 | Lindquist et al. | |
| 2006/0147902 A1 | 7/2006 | Lindquist et al. | |

FOREIGN PATENT DOCUMENTS

| | | |
|---|---|---|
| EP | 1328814 | 10/2006 |
| JP | 2001-501802 | 2/2001 |
| WO | WO 91/04339 | 4/1991 |
| WO | WO 91/05044 | 4/1991 |
| WO | WO 93/03369 | 2/1993 |
| WO | WO 96/39834 | 12/1996 |
| WO | WO 97/37645 | 10/1997 |
| WO | WO 99/06545 | 2/1999 |
| WO | WO 99/62548 | 12/1999 |
| WO | WO 01/02552 | 1/2001 |
| WO | WO 01/06989 | 2/2001 |
| WO | WO 01/23412 | 4/2001 |
| WO | WO 02/35237 | 5/2002 |
| WO | WO 02/065136 | 8/2002 |
| WO | WO 2005/005640 | 1/2005 |

OTHER PUBLICATIONS

Hughes SR et al, PNAS, 93:2065-70, Mar. 5, 1996.*
Lazar, Molecular and Cellular Biology, 8(3): 1247-52, Mar. 1988.*
Skolnick et al., Trends in Biotech., 18(1):34-39, 2000.*
Newcombe et al., Biochimica et Biophysica Acta 104:480-486, 1965.*
Patino et al., Science 273:622-26, 1996.*
King et al., PNAS 94(13):6618-22, Jun. 24, 1997.*
Selvaggini et al., Biochem. Biophys. Res. Comm., 194(3):1380-86, 1993.*
Ogawa et al., PNAS 92(25):11899-903, 1995.*
Schilthuis et al., EMBO J., 12(9):3459-66, 1993.*
Mohler et al., Somatic Cell & Mol. Genet., 20(3):153-62, 1994.*
Rieger et al., Nature medicine, (Dec. 1, 1997) vol. 3, No. 12, pp. 1383-8.*
Haass et al., 1993, Cell, vol. 75, pp. 1039-1042.*
Kretzschmar et al., 1986, DNA, vol. 5, No. 4, pp. 315-324.*
Baker et al., "Induction of β(A4)-amyloid in primates by injection of alzheimer's disease brain homogenate", *Mol. Neurobiol.*, 8(1):25-39, 1994.
Bendheim et al., "Antibodies to a scrapie prion protein", *Nature*, 310(5976):418-421, 1984.
Bertoni et al., "Familial creutzfeldt-jakob disease with the PRNP codon $200^{lys}$ mutation and supranuclear palsy but without myoclonus or periodic EEG complexes", *Neurology*, Abstract, 42(4, Suppl. 3):350, 1992.
Bessen et al., "Non-genetic propagation of strain-specific properties of scrapie prion protein", *Nature*, 375:698-700, 1995.
Bessen et al., "In situ formation of protease-resistant prion protein in transmissible spongiform encephalopathy-infected brain slices", *J. Biol. Chem.*, 272(24):15227-15233, 1997.

(Continued)

*Primary Examiner*—Olga N Chernyshev
(74) *Attorney, Agent, or Firm*—Fish & Richardson P.C.

(57) ABSTRACT

The present invention provides a yeast cell based system for determining factors that control the folding of amyloid proteins of diverse origins. Further the present invention provides methods of using such a system to screen for reagents that affect amyloid formation, a process that is integral to several devastating human disease including Creutzfeld-Jacob disease (CJD), fatal familial insomnia (FFI), Gertsmann-Straussler-Scheinker (GSS) syndrome, and kuru. The system of the present invention provides a rapid screening system to quickly and cheaply identify reagents that affect the folding and aggregation properties of the target protein.

30 Claims, 8 Drawing Sheets

OTHER PUBLICATIONS

Figure 2A:
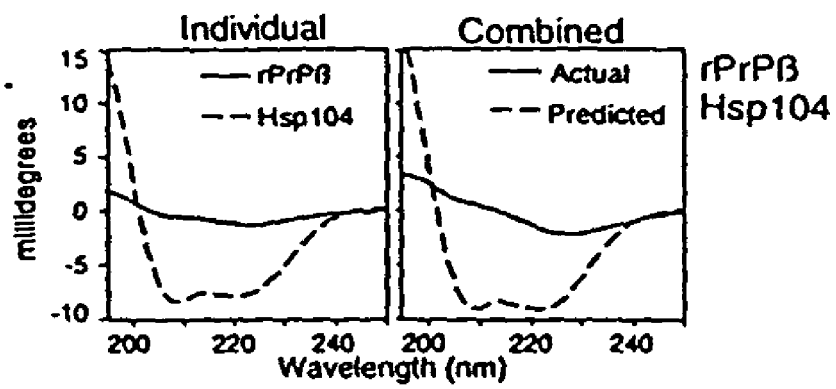

Bockman et al., "Creutzfeld-Jakob disease prion proteins in human brains", *N. Engl. J. Med.*, 312(2):73-78, 1985.
Bolton et al. ",Isolation and structural studies of the intact scrapie agent protein", *Arch. Biochem. Biophys.*, 258:579-590, 1987.
Bolton et al., "Molecular characteristics of the major scrapie prion protein", *Biochemistry* 23:5898-5905, 1984.
Bolton et al., "Identification of a protein that purifies with the scrapie prion", *Science*, 218:1309-1311, 1982.
Borchelt et al., "Evidence for synthesis of scrapie prion proteins in the endocytic pathway", *J. Biol. Chem.*, 267(23):16188-16199, 1992.
Bossers et al., "Scrapie susceptibility-linked polymorphisms modulate the in vitro conversion of sheep prion protein to protease-resistant forms", *Proc. Natl. Acad. Sci. USA*, 94:4931-4936, 1997.
Burston et al., "Release of both native and non-native proteins from a *cis*-only GroEL ternary complex", *Nature*, 383:96-99, 1996.
Buchner, "Supervising the fold: functional principles of molecular chaperones", *FASEB J.*, 10:10-19, 1996.
Carlson et al., "Genetics and polymorphism of the mouse prion gene complex: Control of scrapie incubation time", *Mol. Cell. Biol.*, 8(12):5528-5540, 1988.
Caughey et al., "Binding of the protease-sensitive form of prion protein PrP to sulfated glycosaminoglycan and congo red", *J. Virol.*, 68(4):2135-2141, 1994.
Caughey and Chesebro, "Prion protein and the transmissible spongiform encephalopathies", *Trends Cell Biol.*, 7:56-62, 1997.
Caughey et al., "Secondary structure analysis of the scrapie-associated protein PrP 27-30 in water by infrared spectroscopy", *Biochemistry*, 30:7672-7680, 1991.
Caughey et al., "N-terminal truncation of the scrapie-associated form of PrP by lysosomal protease(s): Implications regarding the site of conversion of PrP to the protease-resistant state", *J. Virol.*, 65(12):6597-6603, 1991.
Caughey and Raymond, "The scrapie-associated form of PrP is made from a cell surface precursor that is both protease- and phospholipase-sensitive", *J. Biol. Chem.*, 266(27):18217-18233, 1991.
Chernoff et al., "Role of the chaperone protein Hsp104 in propagation of the yeast prion-like factor [PSI+]", *Science*, 268:880-884, 1995.
Cyr et al., "Regulation of Hsp70 function by a eukaryotic DnaJ homolog", *J. Biol. Chem.*, 267(29):20927-20931, 1992.
Deb Burman et al., "Chaperone-supervised conversion of prion protein to its protease-resistant form", *Proc. Natl. Acad Sci. USA*, 94:13938-13943, 1997.
Dlouhy et al., "Linkage of the Indiana kindred of Gerstmann-Sträussler-Scheinker disease to the prion protein gene", *Nat. Genet.*, 1:64-67, 1992.
Doh-ura et al., "Pro→Leu change at position 102 of prion protein is the most common but not the sole mutation related to Gerstmann-Sträussler syndrome", *Biochem. Biophys. Res. Commun.*, 163(2):974-979, 1989.
Edenhofer et al., "Prion protein PrP$^c$ interacts with molecular chaperones of the Hsp60 family", *J. Virol.*, 70(7):4724-4728, 1996.
Freeman et al. "Identification of a regulatory motif in Hsp70 that affects ATPase activity, substrate binding and interaction with HDJ-1", *EMBO J.*, 14(10):2281-2292, 1995.
Gabizon et al., "Mutation and polymorphism of the prion protein gene in Libyan Jews with Creutzfeldt-Jakob disease (CJD)", *Am. J. Hum. Genet.*, 53:828-835, 1993.
Gasset et al., "Predicted α-helical regions of the prion protein when synthesized as peptides form amyloid", *Proc. Natl. Acad. Sci. USA*, 89:10940-10944, 1992.
Goldfarb et al., "An insert mutaiton in the chromosome 20 amyloid precursor gene in a Gerstmann-Sträussler-Scheinker family", *J. Neurol. Sci.*, 111:189-194, 1992.
Goldfarb et al., "New mutaiton in scrapie amyloid precursor gene (at codon 178) in Finnish Creutzfeldt-Jakob kindred", *Lancet*, 337:425, 1991.
Goldfarb et al., "Mutation in codon 200 of scrapie amyloid precursor gene linked to Creutzfeldt-Jakob disease in Sephardic Jews of Libyan and non-Libyan origin", *Lancet*, 336:637-638, 1990.

Goldgaber et al., "Mutations in familial Creutzfeldt-Jakob disease and Gerstmann-Sträussler-Scheinker's syndrome", *Exp. Neurol.*, 106:204-206, 1989.
Griffith, "Nature of the scrapie agent", *Nature*, 215:1043-1044, 1967.
Guiroy et al., "Immunolocalization of scrapie amyloid in non-congophilic, non-birefringent deposits in golden Syrian hamsters with experimental transmissible mink encephalopathy", *Neurosci. Lett.*, 155(1):112-115, 1993.
Hartl, "Molecular chaperones in cellular protein folding", *Nature*, 381:571-580, 1996.
Hsiao et al., "Linkage of a prion protein missense variant to Gerstmann-Sträusller syndrome", *Nature*, 338:342-345, 1989.
Hwang et al., "Protease Ti, a new ATP-dependent protease in *Escherichia coli*, contains protein-activated ATPase and proteolytic functions in distinct subunits", *J. Biol. Chem.*, 263(18):8727-8734, 1988.
Kenward et al., "Heat shock proteins, molecular chaperones and the prion encephalopathies", *Cell Stress & Chaperones*, 1(1):18-22, 1996.
King et al., "Prion-inducing domain 2-114 of yeast Sup35 protein transforms in vitro into amyloid-like filaments", *Proc. Natl. Acad. Sci. USA*, 94:6618-6622, 1997.
Kitamoto et al., "An amber mutaiton of prion protein in Gerstmann-Sträussler syndrome with mutant PrP plaques", *Biochem. Biophys. Res. Commun.*, 192(2):525-531, 1993.
Kitamoto et al., "Novel missense variants of prion protein in creutzfeldt-jakob disease or gerstmann-straussler syndrome", *Biochem. Biophys. Res. Commun.*, 191:709-714, 1993.
Klunk et al., "Quantitative evaluation of congo red binding to amyloid-like proteins with a Beta-pleated sheet conformation", *J. Histochem. Cytochem.*, 37(8):1273-1279, 1989.
Kocisko et al., "Cell-free formation of protease-resistant prion protein", *Nature*, 370:471-474, 1994.
Kocisko et al., Species specificity in the cell-free conversion of prion protein to protease-resistant forms: A model for the scrapie species barrier, *Proc. Natl. Acad. Sci. USA*, 92:3923-3927, 1995.
Lansbury and Caughey, "The chemistry of scrapie infection: implications of the 'ice 9' metaphore", *Chem. Biol.*, 2:1-5, 1995.
Lanzetta et al., "An improved assay for nanomole amounts of inorganic phosphate", *Analyt. Biochem.*, 100:95-97, 1979.
Lee et al., "Structure and in vitro molecular chaperone activity of cytosolic small heat shock proteins from Pea", *J. Biol. Chem.*, 270(15):10432-10438, 1995.
Lehmann and Harris, "Mutant and infectious prion proteins display common biochemical properties in cultured cells", *J. Biol. Chem.*, 271(3):1633-1637, 1997.
Lindquist, "Mad cows meet Psi-chotic yeast: The expansion of the prion hypothesis", *Cell*, 89:495-498, 1997.
Masters et al., "Creutzfeldt-Jakob disease: Patterns of worldwide occurrence and the significance of familial and sporadic clustering", *Ann. Neurol.*, 5(2):177-188, 1979.
Maurizi et al., "Endopeptidase Clp: ATP-dependent Clp protease from *Escherichia coli*", *Meth. in Enzymol.*, 244:314-331, 1994.
McKinley et al., "A protease-resistant protein is a structural component of the scrapie prion", *Cells*, 35:57-62, 1982.
Medori et al., *N. Engl. J. Med.*, 326:444-449, 1992.
Mehlhorn et al., "High-level expression and characterization of a purified 142-residue polypeptide of the prion protein", *Biochemistry*, 35(17):5528-5537, 1996.
Mendoza et al., "Chaperonins facilitate the in vitro folding of monomeric mitochondrial rhodanese", *J. Biol. Chem.*, 266(20):13044-13049, 1991.
Müller-Hill and Beyreuther, "Molecular biology of alzheimer's disease", *Annu. Rev. Biochem.*, 58:287-307, 1989.
Nakamura et al., "L-proline is an essential amino acid for hepatocyte growth in culture", *Biochem. Biophys. Res. Comm.*, 122(3):884-891, 1984.
Nguyen et al., "Prion protein peptides induce α-helix to β-sheet conformational transitions", *Biochemistry*, 34:4186-4192, 1995.
Oesch et al., "A cellular gene encodes scrapie PrP 27-30 protein", *Cell*, 40:735-746, 1985.

Pan et al., "Conversion of α-helices into β-sheets features in the formation of the scrapie prio proteins", *Proc. Natl. Acad. Sci. USA,* 90:10962-10966, 1993.

Parsell et al., "*Saccharomyces cerevisiae* Hsp104 protein", *J. Biol. Chem.,* 269(6):4480-4487, 1994.

Parsell et al., "Protein disaggregation mediated by heat-shock protein Hsp104", *Nature,* 372:475-478, 1994.

Parsell et al., "Hsp104 is a highly conserved protein with two essential nucleotide-binding sites", *Nature,* 353:270-272, 1991.

Parsell and Lindquist, "The function of heat-shock proteins in stress tolerance: degradation and reactivation of damaged proteins", *Annu. Rev. Genet.,* 27:437-496, 1993.

Patino et al., "Support for the prion hypothesis for inheritance of a phenotypic trait in yeast", *Science,* 273:622-626, 1996.

Paushkin et al., "Propagation of the yeast prion-like [*psi*⁺] determinant is mediated by oligomerization of the *SUP35*-encoded polypeptide chain release factor", *EMBO J.,* 15(12):3127-3134, 1996.

Paushkin et al., "In vitro propagation of the prion-like state of yeast Sup35 protein", *Science,* 277:381-383, 1997.

Petersen et al., "Analysis of the prion protein gene in thalamic dementia", *Neurology,* 42:1859-1863, 1992.

Pike et al., "Neurodegeneration induced by β-amyloid peptides in vitro: The role of peptide assembly state", *J. Neurosci.* 13(4):1676-1687, 1993.

Poulter et al., "Inherited prion disease with 144 base pair gene insertion", *Brain,* 115:675-685, 1992.

Prusiner et al., "Purification and structural studies of a major scrapie prion protein", *Cell,* 38:127-134, 1984.

Prusiner et al., "Further purification and characterization of scrapie prions", *Biochemistry,* 21:6942-6950, 1982.

Prusiner, "Prions", *In: Fields Virology,* Fields, B.N., Knipe, D.M. & Howley, P.M. (Eds.), Lippencott-Raven Publishers, Philadelphia, pp. 2901-2950, 1996.

Prusiner et al., "Scrapie prions aggregate to form amyloid-like birefringent rods", *Cell,* 35:349-358, 1983.

Prusiner, "Molecular biology and pathogenesis of prion diseases", *Trends Biochem. Sci.,* 21:482-487, 1996.

Raymond et al., "Molecular assessment of the potential transmissibilities of BSE and scrapie to humans", *Nature,* 388:285-288, 1997.

Riek et al., "NMR structure of the mouse prion protein doman PrP (121-231)", *Nature,* 382:180-184, 1996.

Sanchez and Lindquist, "HSP104 required for induced thermotolerance", *Science,* 248:1112-1115, 1990.

Schirmer and Lindquist, "Interactions of the chaperone Hsp104 with yeast Sup35 and mammalian PrP", *Proc. Natl. Acad. Sci. USA,* 94:13932-13937, 1997.

Schirmer et al., "HSP100/Clp proteins: A common mechanism explains diverse functions", *Trends Biochem. Sci.,* 21:289-296, 1996.

Talzelt et al., "Chemical chaperones interfere with the formation of scrapie prion protein", *EMBO J.,* 15(23):6363-6373, 1996.

Tashima et al., "Congophilia in cerebral amyloidosis is modified by inactivation procedures on slow transmissible pathogens", *Brain Res.,* 399(1):80-86, 1986.

Telling et al., "Prion propagation in mice expressing human and chimeric PrP transgenes implicates the interaction of cellular PrP with another protein", *Cell,* 83:79-90, 1995.

Ter-Avanesyan et al., "Deletion analysis of the *SUP35* gene of the yeast *Saccharomyces cerevisiae* reveals two non-overlapping functional regions in the encoded protein", *Mol. Microb.,* 7(5):683-692, 1993.

Todd and Lorimer, "Stability of the asymmetric *Escherichia coli* chaperonin complex", *J. Biol. Chem.,* 270(10):5388-5394, 1995.

Vey et al., "Subcellular colocalization of the cellular and scrapie prion proteins in caveolae-like membranous domains", *Proc. Natl. Acad. Sci. USA,* 93:14945-14949, 1996.

Wawrzynow et al., "The ClpX heat-shock protein of *Escherichia coli*, the ATP-dependent substrate specificity component of the ClpP-ClpX protease, is a novel molecular chaperone", *EMBO. J.,* 14(9):1867-1877, 1995.

Welch and Brown, "Influence of molecular and chemical chaperones on protein folding", *Cell Stress & Chaperones,* 1(2):109-115, 1996.

Wickner et al., "A molecular chaperone, ClpA, functions like DnaK and DnaJ", *Proc. Natl. Acad. Sci. USA,* 91:12218-12222, 1994.

Wickner, "[URE3] as an altered *URE2* protein: Evidence for a prion analog in *Saccharomyces cerevisiae*", *Science,* 264:566-569, 1994.

Wu and Chen, "Adsorption of proteins onto glass surfaces and its effect on the intensity of circular dichroism spectra", *Analyt. Biochem.,* 177:178-182, 1989.

Yancey et al., "Living with water stress: Evolution of osmolyte systems", *Science,* 217:1214-1222, 1982.

Zeigelhoffer et al., "The dissociation of ATP from hsp70 of *Saccharomyces cerevisiae* is stimulated by both Ydj1p and peptide substrates", *J. Biol. Chem.,* 270(18):10412-10419, 1995.

Zhang et al., "Conformational transitions in peptides containing two putative α-helices of the prion protein", *J. Mol. Biol.,* 250:514-526, 1995.

Zhang et al., "Physical studies of conformational plasticity in a recombinant prion protein", *Biochemistry,* 36:3543-3553, 1997.

Patent Cooperation Treaty Search Report, May 21, 1999.

Masison and Wickner, "Prion-Inducing Domain of Yeast Ure2p and Protease Resistance of Ure2p in Prion Containing Cells," *Science* 270, 93-95, Abstract, 1995.

Tuite and Lindquist, "Maintenance and Inheritance of Yeast Prions," *Trends in Genetics,* 12(11), 467-471, 1996.

Lindquist et al., "Amyloid Fibres of Sup35 Support a Prion-Like Mechanism of Inheritance in Yeast," *Biochem. Soc. Trans.,* 26(3), 486-490, 1998.

Schirmer and Lindquist, "Interactions of the Chaperone Hsp104 with Yeast Sup35 and Mammalian PrP," *Proc. Natl. Acad. Sci.,* 94, 13932-13937, Dec. 1997.

Adams et al., "Methods in Yeast Genetics," A Cold Spring Harbor Laboratory Course Manual, 1997.

Andoh et al., "Yeast Glycogen Synthase Kinase 3 is Involved in Protein Degradation in Cooperation with Bul1, Bul2, and Rsp5," Moll. Cell. Biol., 20(18):6712-6720 (2000).

Baumann et al., "Abnormal Alzheimer-Like Phosphorylation of Tau-Protein by Cyclin-Dependent Kinases cdk2 and cdk5," FEBS Lett., 336(3):417-424 (1993).

Billingsley et al., "Regulated Phosphorylation and Dephosphorylation of Tau Protein: Effects on Microtubule Interaction, Intracellular Trafficking and Neurodegeneration," Biochem. J., 323:577-591 (1997).

Borkovich et al,, "hsp82 is an essential protein that is required in higher concentrations for growth of cells at higher temperatures," Mol Cell Biol. 9:3919-3930, 1989.

Boucherie et al., "Differential synthesis of glyceraldehyde-3-phosphate dehydrogenase polypeptides in stressed yeast cells," FEMS Microbiol Lett., 125:127-133, 1995.

Burke et al., "Huntingtin and DRPLA proteins selectively interact with the enzyme GAPDH," Nat Med. 2:347-350, 1996.

Cafferty, Patrick W., "Characterization of Glycogen Synthase Kinase 3 Beta and Tau Interaction," Dept. of Neurology and Neurosurgery, McGill University (2000).

Chai et al., "Analysis of the role of heat shock protein (Hsp)molecular chaperones in polyglutamine disease," J Neurosci., 19:10338-10347, 1999.

Chai et al., "Evidence for proteasome involvement in polyglutamine disease: localization to nuclear inclusions in SCA3/MJD and suppression of polyglutamine aggregation in vitro," Hum Mol Genet., 8:673-682, 1999.

Chen and Hochstrasser, "Biogenesis, structure and function of the yeast 20S proteasome," Embo J., 14:2620-2630, 1995.

Cooper et al., "α-Synuclein Blocks ER-Golgi Traffic and Rab I Rescues Neuron Loss in Parkinson's Models," *Science,* 313:324-328 (2006).

Crauwels et al., "The Sch9 Protein Kinase in the Yeast *Saccharomyces cerevisiae* Controls cAPK Activity and is Required for Nitrogen Activation of the Fermentable-Growth-Medium-Induced (FGM) Pathway," Microbiology, 143:2627-2637 (1997).

Cummings et al., "Chaperone suppression of aggregation and altered subcellular proteasome localization imply protein misfolding in SCA1," Nat Genet., 19:148-154, 1998.

DeMarini et al., "The yeast SEN3 gene encodes a regulatory subunit of the 26S proteasome complex required for ubiquitin-dependent protein degradation in vivo," Mol Cell Biol., 15:6311-6321, 1995.

Engelender et al., "Synphilin-1 associates with α-synuclein and promotes the formation of cytosolic inclusions," Nature Genetics, 22:110-114 (1999).

Escher et al., "Taking Yeast from the Brewery to Drug Discovery," Chimia, 54(4):171-173 (2000).

Gething, Guidebook to molecular chaperones and protein folding catalysts. Oxford University Press, 1997.

Geyskens et al., "Expression of Mammalian PKB Partially Complements Deletion of the Yeast Protein Kinase Sch9," NATO Science Series, A316:117-126 (2000).

Hartley et al., "The Yak1 Protein Kinase of *Saccharomyces Cerevisiae* Moderates Thermotolerance and Inhibits Growth by an Sch9 Protein Kinase-Independent Mechanism," Genetics, 136:465-474 (1994).

Huang et al., "Mammalian Cdk5 is a Functional Homologue of the Budding Yeast Pho85 Cyclin-Dependent Protein Kinase," Proc. Natl. Acad. Sci. USA, 96(25):14445-14450 (1999).

Jana et al., "Polyglutamine length-dependent interaction of Hsp40 and Hsp70 family chaperones with truncated N-terminal huntingtin: their role in suppression of aggregation and cellular toxicity," Hum Mol Genet., 9(13):2009-2018, 2000.

Kazantsev et al., "Insoluble detergent-resistant aggregates form between pathological and nonpathological lengths of polyglutamine in mammalian cells," Proc Natl Acad Sci U.S.A., 96: 11404-1 1409, 1999.

Kilmartin et al., "Structural Rearrangements of Tubulin and Actin During the Cell Cycle of the Yeast Saccharomyces," *J. Cell Biol.*, 98:922-933 (1984).

Kimura et al., "Role of the protein chaperone YDJ1 in establishing Hsp90-mediated signal transuction pathways," Science, 268:1362-1365, 1995.

Koo et al., "Amyloid diseases: Abnormal protein aggregation in neurodegeneration," PNAS 96:9989-9990, 1999.

Krobitsch and Lindquist, "Aggregation of huntingtin in yeast varies with the length of the polyglutamine expansion and the expression of chaperone proteins," Proc Natl Acad Sci U.S.A., 97(4):1589-1594, 2000.

Lindquist, Susan, "Yeast as a Model System for Studying Parkinson's Disease," Grant No. 1R21NS044829-01, (Abstract Only) (2004).

Liu et al., "Oligopeptide-Repeat Expansions Modulate 'Protein-Only' Inheritance in Yeast" Nature 400:573-576 (1999).

Mawal-Dewan, "Phosphorylation of Tau Protein by Purified p34$^{cdc28}$ and a Related Protein Kinase from Neurofilaments," J. Biol. Chem., 267(27):19705-19709 (1992).

Moore et al., "Triplet repeats form secondary structures that escape DNA repair in yeast," Proc. Natl. Acad. Sci. U.S.A., 96:1504-1509, 1999.

Muchowski et al., "Hsp70 and Hsp40 chaperones can inhibit self-assembly of polyglutamine proteins into amyloid-like fibrils," Proc. Natl. Acad. Sci. USA, 97:7841-7846, 2000.

Mumberg et al., "Regulatable promoters of *Saccharmoyce cerevisiae*: comparison of transcriptional activity and their use for heterologous expression," Nucleic Acids Res. 22:5767-5768, 1994.

Mumberg et al., "Yeast vectors for the controlled expression of heterolgous proteins in different genetic backgrounds," Gene. 156:119-122, 1995.

Nathan and Lindquist, "Mutational analysis of HspPO function: interactions with a steroid receptor and a protein kinase," Mol Cell Biol. 15:3917-3925, 1995.

Nathan et al., "Identification of SSF1, CNS1, and HCH1 as multicopy suppressors of a *Saccharomyces cerevisiae* Hsp90 loss-of-function mutation," Proc. Natl. Acad. Sci. U.S.A. 96:1409-1414, 1999.

Neystat et al., "Analysis of Synphilion-1 and Synuclein Interactions by Yeast Two-Hybrid β-Galactosidase Liquid Assay," Neuroscience Letters, vol. 325, 2002, pp. 119-123.

Neystat et al., "Identification of alpha-synuclein interacting proteins in rat brain by yeast two-hybrid screen," Database Biosis (Online), Biosciences Information Services, XP-002431841, Database Accession No. PREV200100070267, Society for Neuroscience Abstracts, 26:1-2, 2000. oc Apr. 29, 2010.

Notice of Opposition, filed by FoldRx Pharmaceuticals, Inc. against European Patent No. 1373529, Jan. 22, 2009.

Notice of Opposition, filed by ReMYND NV against European Patent No. 1392849, Oct. 2, 2008.

Ostrerova et al., "α-Synuclein shares physical and functional homology with 14-3-3 proteins," J. Neuroscience, 19(14):5782-5791(1999).

Ostrerova-Golts et al., "The A53T α-Synuclein Mutation Increases Iron-Dependent Aggregation and Toxicity," J. Neuroscience, 20(16):6048-6054 (2000).

Outeiro et al., "Yeast Cells Provide Insights into Alpha-Synuclein Biology and Pathobiology," Science, 302:1772-1775 (2003).

Petko et al., "Hsp26 is not required for growth at high temperatures, nor for thermotolerance, spore development, or germination," Cell., 45:885-894, 1986.

Pringle et al., "Staining of Bud Scars and Other Cell Wall Chitin with Calcofluor," J. Meth. Enzym., 194:732 (1981).

Proprietor's Observations to the European Patent Office on the Opposition filed by ReMynd NV against EP 1392849 B1, dated Jun. 25, 2009.

Proprietor's Observations to the European Patent Office on the opposition filed by FoldRx against EP 1373529 B1, dated Sep. 2, 2009.

Puziss et al., "MDS1, a Dosage Suppressor of an *mck1*Mutant, Encodes a Putative Yeast Homolog of Glycogen Synthase Kinase 3," Molecular and Cellular Biology, 14:831-839 (1994).

Richardson et al., "Mouse Models of Alzheimer's Disease: A Quest for Placques and Tangles," ILAR Journal, 43:89-99 (2002).

Saudou et al., "Huntingtin acts in the nucleus to induce apoptosis but death does not correlate with the formation of intranuclear inclusions," Cell., 95:55-66, 1998.

Schweitzer et al., "Destabilization of CAG trinucleotide repeat tracts by mismatch repair mutations in yeast," Hum Mol Genet. 6:349-355, 1997.

Song et al., "Proteolytic Processing and Degradation of Human Presenilin-1 Expressed in Yeast," Neuroscience Letters, 282:65-68 (2000).

Spillantini MG et al., *Nature*, 388:839-40, 1997.

Stenoien et al., "Polyglutamine-expanded androgen receptors form aggregates that sequester heat shock proteins, proteasome components and SRC-1, and are suppressed by the HDJ-2 chaperone," Hum Mol Genet., 8:731-741, 1999.

Stone and Craig, "Self-regulation of 70-kilodalton heat shock proteins in *Saccharomyces cerevisiae*," Mol Cell Biol., 10:1622-1632, 1990.

Tanaka et al., "Inducible Expression of Mutant α-Synuclein Decreases Proteasome Activity and Increases Sensitivity to Mitochondria-Dependent Apoptosis," Human Molecular Genetics, 2001, vol. 10, No. 9, pp. 919-926.

Temussi et al., "From Alzheimer's to Huntington: why is a structural understanding so difficult," EMBO Journal 22(3):355-361, 2003.

Thevelein, J.M., "Signal Transduction in Yeast," Yeast, 10:1753-1790 (1994).

Vogel et al., "Heat-shock proteins Hsp104 and Hsp70 reactivate mRNA splicing after heat inactivation," Current Biology, 5:306-317, 1995.

Vonsattel et al., "Neuropathological classification of huntington's disease," J Neuropathol Exp Neurol., 44:559-577, 1985.

Willingham et al., "Yeast Genes That Enhance the Toxicity of a Mutant Huntingtin Fragment or α-Synuclein," Science, 302:1769-1772 (2003).

Woods et al., "The Kinase DYRK Phosphorylates Protein-Synthesis Initiation Factor eIF2Bε at Ser$^{539}$ and the Microtubule-Associated Protein tau at Thr$^{212}$: Potential Role for DYRK as a Glycogen Synthase Kinase 3-Priming Kinase," Biochem. J., 355:609-615 (2001).

Yamaguchi et al., "Preferential Labeling of Alzheimer Neurofibrillary Tangles with Antisera for Tau Protein Kinase (TPK) I/Glycogen Synthase Kinase-3β and Cyclin-Dependent Kinase 5, a component of TPK II," Acta Neuropathol., 92:232-241 (1996).

Yan et al., "Membrane Receptors, Sensors and Transporters," Yeast, 18(S1):S273 (2001).

Zhang et al., "Interaction of the E1A Oncoprotein with Yak1p, a Novel Regulator of Yeast Pseudohyphal Differentiation, and Related Mammalian Kinases," Molecular Biology of the Cell, 12:699-710 (2001).

Zhou et al., "Pini-Dependent Prolyl Isomerization Regulates Dephosphorylation of Cdc25C and Tau Proteins," Molecular Cell, 6:873-883 (2000).

* cited by examiner

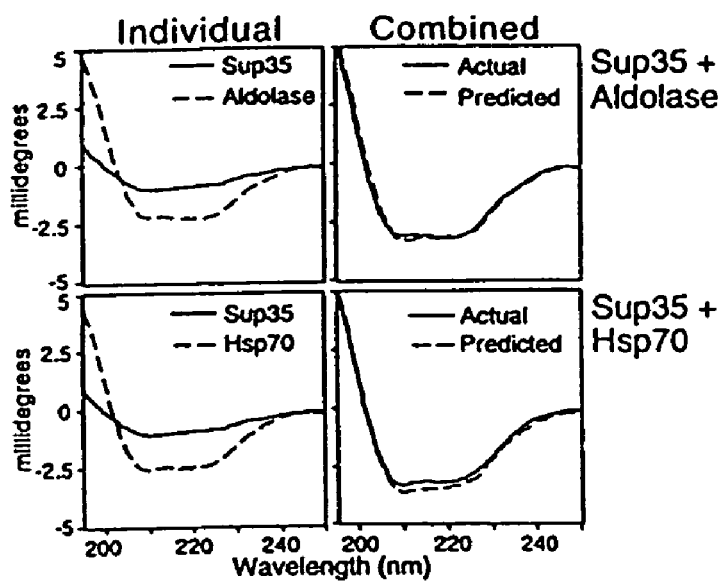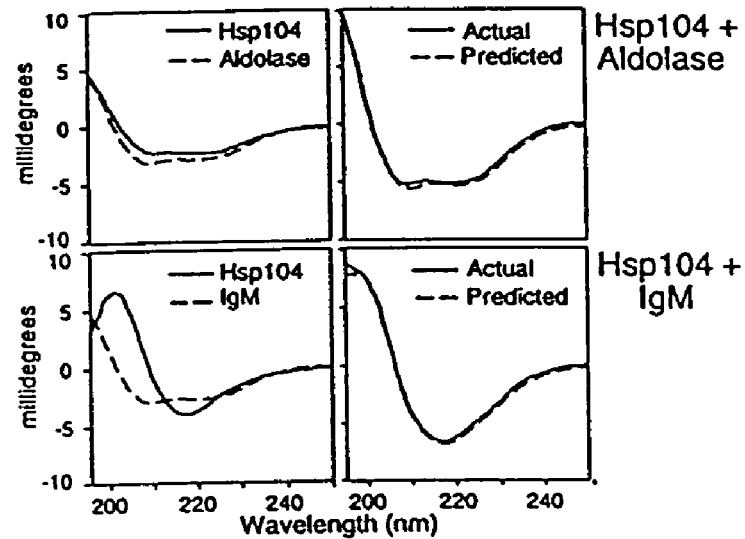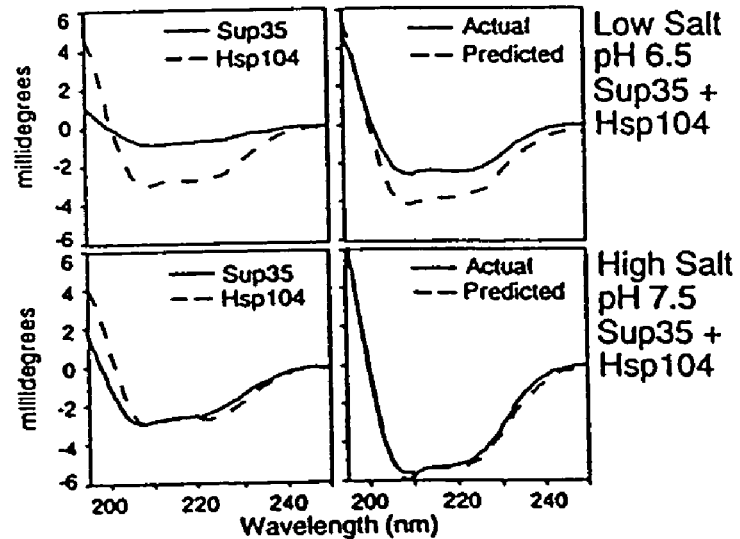

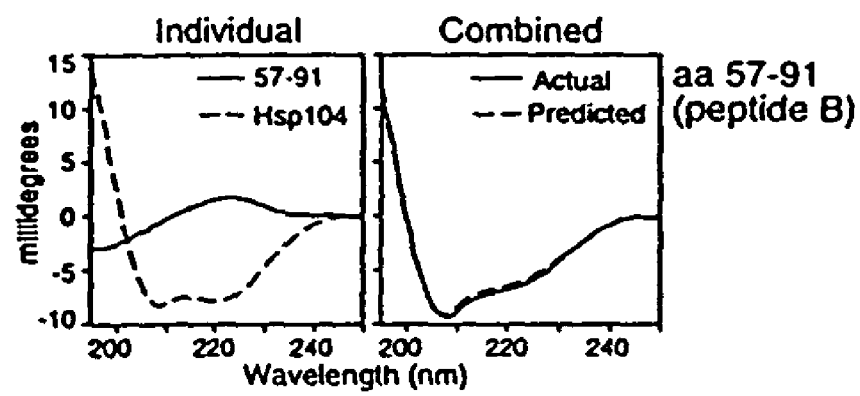
FIG. 4A. aa 57-91 (peptide B)
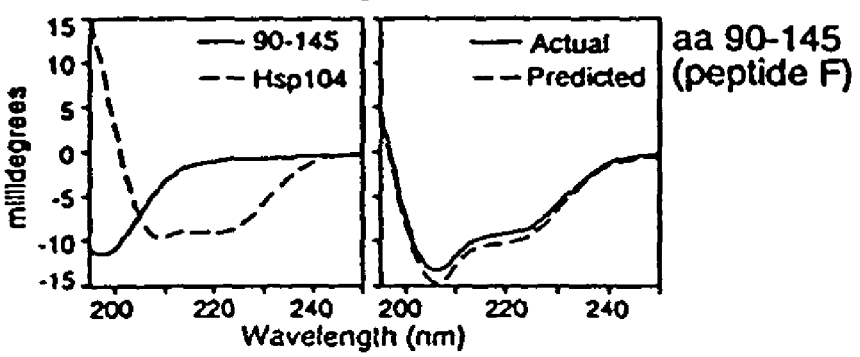
FIG. 4B. aa 90-145 (peptide F)
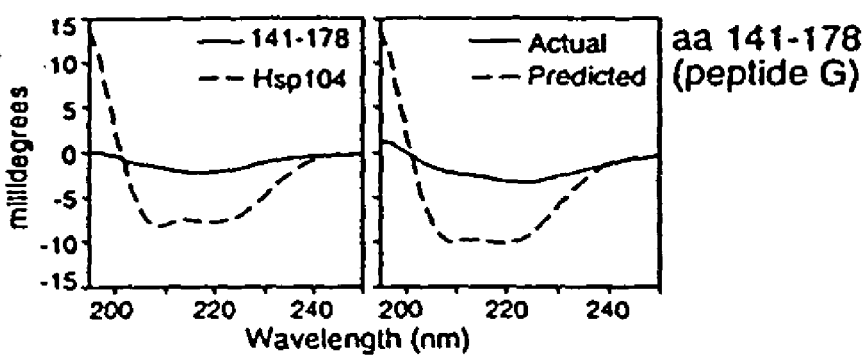
FIG. 4C. aa 141-178 (peptide G)
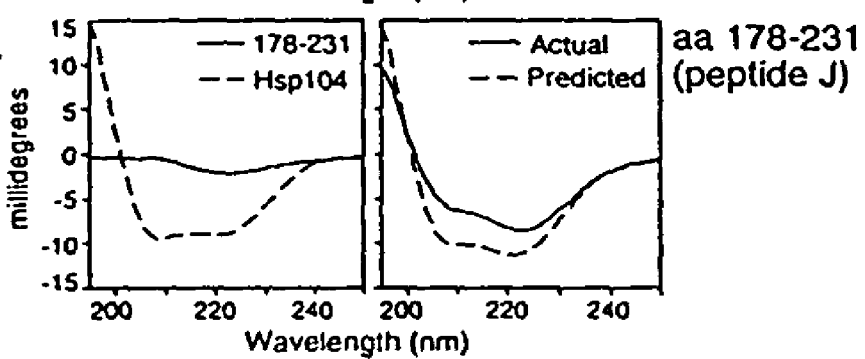
FIG. 4D. aa 178-231 (peptide J)

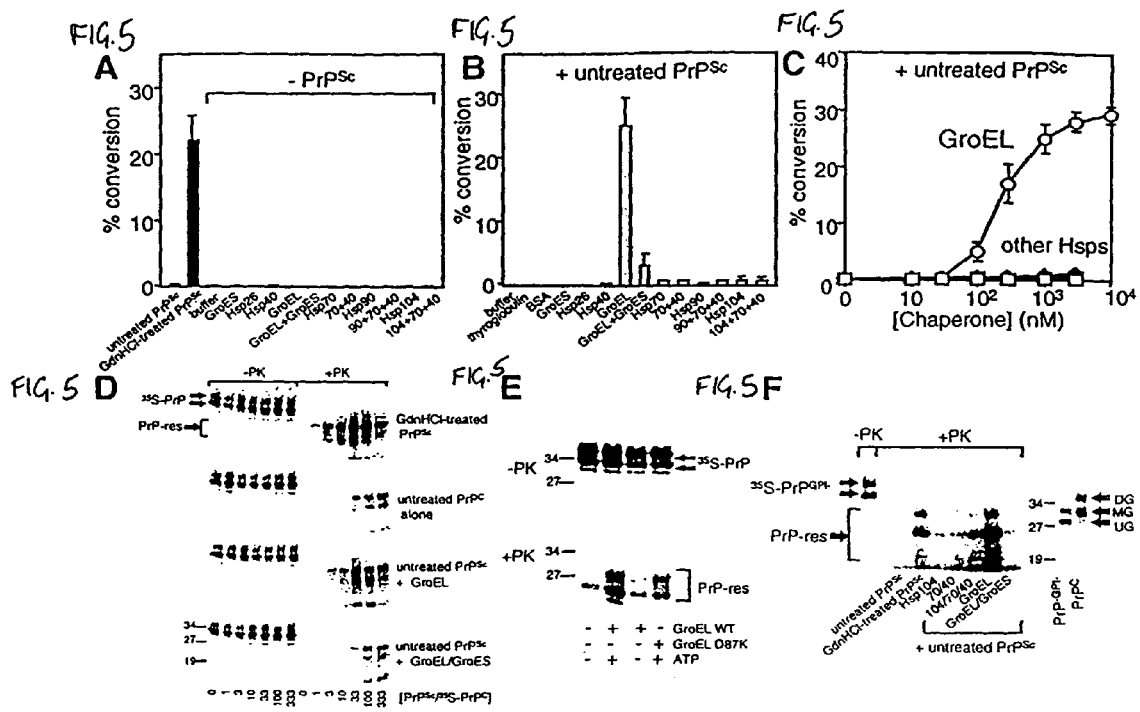

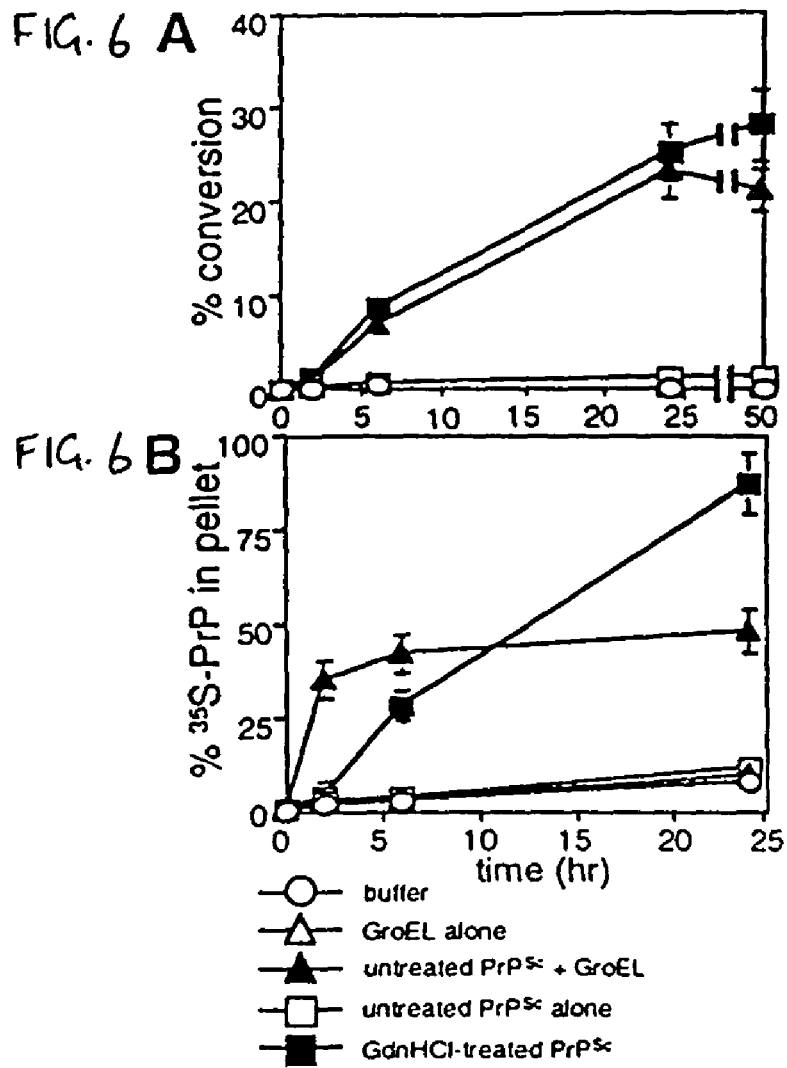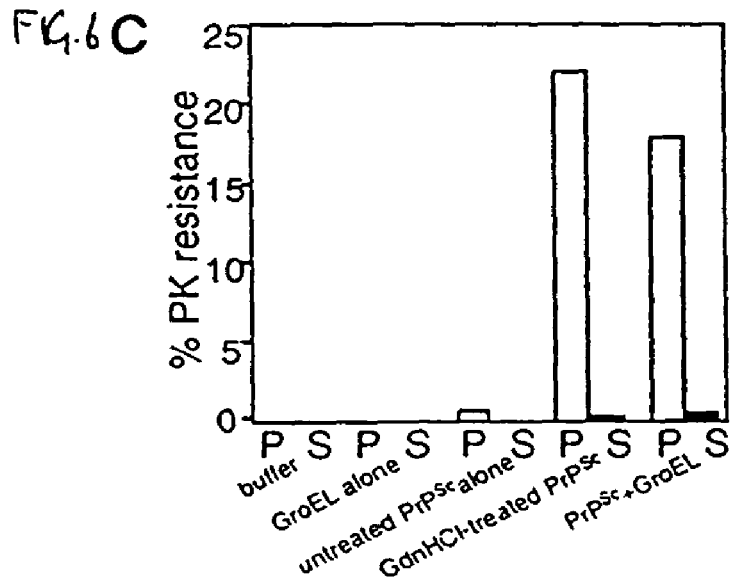

METHODS FOR IDENTIFYING FACTORS THAT CONTROL THE FOLDING OF AMYLOID PROTEINS OF DIVERSE ORIGIN

The present application is a continuation of provisional application Ser. No. 60/069,168 filed Dec. 9, 1997, and provisional application Ser. No. 60/084,824, filed May 8, 1998, the entire disclosure of each of which is incorporated herein by reference without disclaimer.

The U.S. government owns rights in the present invention pursuant to grant number NIH GM 25874 from the National Institutes of Health.

1.0 BACKGROUND OF THE INVENTION

1.1 Field of the Invention

The present invention relates generally to the fields of genetics and cellular biology. More particularly, it concerns a yeast based system for the determination of compounds that affect amyloid formation. The present invention relates to the determination of compounds that affect the amyloid associated with Alzheimer's disease, Transmissible spongiform encephalopathies (TSEs), and several rare human neuropathies: Creutzfeld-Jacob disease (CJD), fatal familial insomnia (FFI), Gertsmann-Straussler-Scheinker (GSS) syndrome, and kuru.

1.2 Description of Related Art

1.2.1 Yeast Prions

Recently, a novel mode of inheritance has been discovered in *Saccharomyces cerevisiae* (Wickner, 1994; Lindquist, 1997). Phenotypes transmitted by two dominant, cytoplasmically inherited genetic elements, [PSI+] and [URE3], seem to depend upon the inheritance of altered protein structures, rather than altered nucleic acids. The "protein-only" hypothesis for their inheritance led these elements to be called "yeast prions" (Wickner, 1994). The term "prion" was first coined to describe the infectious agent hypothesized to cause mammalian spongiform encephalogathies (TSEs) by a "protein only" mechanism: a normal cellular protein ($PrP^C$) adopts an altered conformation ($PrP^{Sc}$) and interacts with other $PrP^C$ proteins to change their conformation as well (Prusiner, 1996).

The yeast [PSI+] element, the subject of the inventor's work, does not generally kill cells. It reduces the fidelity of ribosome translation termination and thereby suppresses nonsense codons (Lindquist, 1997). This phenotype is thought to result from a change in the state of the translation-termination factor, Sup35, that interferes with its normal function. In [psi−] cells, Sup35 is protease sensitive and is mostly soluble; in [PSI+] cells, Sup35 has increased protease resistance and is mostly aggregated (Paushkin et al., 1996; Patino et al., 1996; Paushkin et al., 1997). "Aggregate" is used in a general sense; Sup35 may be polymerized into an amyloid-like structure, or coalesced in a less ordered state. When pre-existing Sup35 is in the aggregated state, newly made Sup35 aggregates too, causing a self-perpetuating loss of function in the termination factor and a heritable change in translational fidelity (Patino et al., 1996; Paushkin et al., 1997).

[PSI+] depends upon the chaperone protein Hsp104. The first known function of Hsp104 was in thermotolerance in yeast, where it increases survival after exposure to extreme temperatures up to 1000-fold (Sanchez and Lindquist, 1990). It does so by promoting the reactivation of proteins that have been damaged by heat and have begun to aggregate (Parsell et al., 1994). At normal temperatures, Hsp104 overexpression cures cells of [PSI+]. Sup35 becomes soluble and the fidelity of translation termination is restored. This state is heritable, even when overexpression of Hsp104 ceases (Chernoff et al., 1995). Because the only known function of Hsp104 is to alter the conformational state of other proteins, these observations provide a strong argument that [PSI−1] is indeed based upon a heritable (self-perpetuating) change in the conformational state of Sup35.

Surprisingly, deletions of HSP104 also cure cells of [PSI+], and Sup35 is soluble in such cells as well (Patino et al., 1996; Chernoff et al., 1995). This is very different from heat-induced aggregates, which remain insoluble in hsp104 deletion strains. Clearly, the relationship between Hsp104 and [PSI−1] is more complex than the relationship between Hsp104 and thermotolerance.

1.2.2 Human Prions

The family of transmissible spongiform encephalopathies (TSEs) include scrapie in sheep, bovine spongiform encephalopathy (BSE) or "mad cow disease" in cattle, and several rare human neuropathies: Creutzfeld-Jacob disease (CJD), fatal familial insomnia (FFI), Gertsmann-Straussler-Scheinker (GSS) syndrome, and kuru (Caughey and Chesebro, 1997; Prusiner, 1996). A central event in TSE pathogenesis is the accumulation in the nervous system of an abnormally-folded version ($PrP^{Sc}$) of a normal cellular protein, $PrP^C$. Griffith first proposed a "protein-only" model to explain the unconventional behavior of the infectious TSE agent (Griffith, 1967). Indeed, the "prion", a term by which the agent is popularly known today, appears to be almost entirely proteinaceous: consisting primarily of $PrP^{Sc}$ (Caughey and Chesebro, 1997; Prusiner, 1996).

Several lines of evidence show that $PrP^C$ is conformationally distinct from $PrP^{Sc}$ although both molecules derive from the same primary sequence and have no detectable post-translational differences (Caughey and Chesebro, 1997; Prusiner, 1996; Caughey et al., 1991; Pan et al., 1993; Riek et al., 1996). The conversion of $PrP^C$ to $PrP^{Sc}$ appears to involve direct interactions of $PrP^C$ with pre-existing $PrP^{Sc}$ (Caughey and Chesebro, 1997; Prusiner, 1996; Kocisko et al., 1994). However, the exact mechanism underlying conversion is not known. Genetic and inhibitor studies have suggested that other cellular factors may influence TSE pathogenesis or serve as regulators of disease (Kenward et al., 1996; Talzelt et al., 1996; Carlson et al., 1988; Caughey et al., 1994; Telling et al., 1995; Edenhofer et al., 1996). None have been conclusively identified; however, cellular osmolytes (sometimes called chemical chaperones; Caughey and Raymond, 1991) and protein chaperones have been frequently speculated to be among them (Kenward et al., 1996; Caughey et al., 1994; Telling et al., 1995; Edenhofer et al., 1996).

2.0 SUMMARY OF THE INVENTION

The chaperone protein Hsp104 controls the genetic behavior of a mysterious yeast prion-like element known as [PSI+]. The chaperone Hsp104 controls the aggregation of Sup35, the protein determinant of [PSI+].

The present invention includes, but is not limited to, the following features:

1) The protein Sup35 forms amyloid-like protein fibers in vitro. This is a property shared by other amyloidogenic proteins that cause human disease.

2) The yeast protein Hsp104 affects the behavior of Sup35 in vitro. It also affects the behavior of PrP (the mammalian prion protein) in vitro in a similar manner and interacts in a specific manner with β-amyloid peptide 1-42 (Alzheimer's disease peptide).

3) When mammalian PrP is expressed in yeast cells, its folding state depends upon the Hsp104 protein. This is the final element that establishes that yeast can provide an excellent model system for studying factors that affect the folding properties of human disease proteins that have an amyloidogenic character.

In important embodiments of the present invention, this yeast system is used in methods of identifying a candidate substance that inhibits the aggregation of an aggregate-prone amyloid protein. Such methods comprise contacting a yeast cell that expresses an aggregate-prone amyloid protein with the candidate substance under conditions effective to allow aggregated amyloid formation, and determining the ability of the candidate substance to inhibit the aggregation of the aggregate-prone amyloid protein.

The term "aggregate-prone amyloid protein" is meant to be any protein that is able to form an amyloid or amyloid-like deposit. Amyloid or amyloid like deposits are generally insoluble fibrillary material. Although many proteins are capable of aggregating at high concentrations, aggregate prone amyloid proteins are able to, and often do, aggregate under physiological conditions, such as inside of a cell. Aggregate-prone amyloid proteins include yeast proteins, such as Sup35 and URE3, and mammalian proteins, such as PrP and β-amyloid polypeptide. The inventors contemplate that a protein of essentially any origin may be used in the present invention.

In some preferred embodiments, the aggregate-prone amyloid protein is a chimeric protein. By "chimeric protein" it is meant that the protein comprises polypeptides that do not naturally occur together in a single protein unit. Preferred chimeric proteins comprises at least the N-terminal domain of Sup35. This domain has been found to form aggregates in yeast and in vitro and is capable of causing, the aggregation of chimeric proteins comprising this domain. Other preferred chimeric proteins include comprises at least an aggregate forming domain of a mammalian amyloid polypeptide, such as at least amino acids 1-42 of the β-amyloid protein or at least the aggregate forming domain of PrP. In an important embodiment, the chimeric protein comprises Sup35 in which the N-terminal domain has been replaced by amino acids 1-42 of β-amyloid protein.

In other embodiments, the chimeric protein comprises at least an aggregate forming domain of an aggregate-prone amyloid protein operably attached to a detectable marker protein. By "operably attached" it is meant that the aggregate forming domain and the marker protein are attached such that the chimeric protein maintains the ability to aggregate and the marker protein maintains the property of allowing detection of aggregation of the chimeric protein. For example, the Sup35 N-terminal domain is operably linked to the green fluorescent protein when this polypeptide is capable of aggregating and the aggregated protein maintains the ability of green fluorescent protein to fluoresce.

In other embodiments, the aggregation of the chimeric protein-leads to loss of function of the marker protein. When the marker protein is an enzyme, aggregation of the marker protein leads to loss of the enzymatic activity of the marker protein. That is to say that the enzymatic marker protein maintains its enzymatic activity when not aggregated, but aggregation leads to the loss of enzymatic activity. Loss of activity may be due to an alteration of the structure of the marker protein or may be due to sequestering of the protein in the aggregates away form the substrate or cofactors. The enzyme may be luciferase, confer drug resistance, or, in preferred embodiments, have the translation termination activity of the Sup35 protein. In other embodiments, the marker protein is a hormone receptor, such as the glucocorticoid receptor.

The inventors contemplate that the aggregation of the aggregate-prone amyloid protein may be detected in a number of ways. Including the methods described above, the aggregate may be detected by staining with Congo Red. In other embodiments, the aggregation is detected by the characteristic protease resistance of the aggregated protein. The ability to detect the protein may be increased by labeling the aggregate-prone amyloid protein. Labels useful in the detection of the aggregate-prone amyloid protein include radioactive isotope labels, such as $^{35}S$, fluorophores, such as green fluorescent protein, or chromophores. In some preferred embodiments, aggregation is determined by the presence of a [PSI+] phenotype.

Although overexpression of the chimeric protein comprising the aggregate-prone domain of an aggregate-prone amyloid protein often leads to aggregation of the chimeric protein, the inventor has found that this aggregation is dependent on expression of heat shock proteins, such as Hsp104. Therefore, conditions effective to allow amyloid formation may involve modulating the expression of Hsp104 in the yeast cell. In preferred embodiments, the yeast cell overexpresses Hsp104.

In other embodiments of the present invention, the yeast systems are used to identify candidate substances for therapeutic activity against an amyloidogenic disease in an animal. These methods comprise contacting a yeast cell that expresses an aggregate-prone amyloid protein with said candidate substance under conditions effective to allow amyloid formation and determining the ability of said candidate substance to inhibit aggregation of the aggregate-prone amyloid protein. Thus, the ability to inhibit aggregation is indicative of therapeutic activity.

Amyloidogenic diseases in animals include Alzheimer's disease, scrapie, spongiform encephalopathy in a mammal, kuru, Creutzfeldt-Jakob disease, Gestmann-Strausser-Scheinker disease, or fatal familial insomnia. In preferred embodiments, one would express a protein comprising the aggregate forming domain of the etiological agent of a particular disease in the yeast system to identify therapeutic compounds for that particular disease. Therefore, in determining therapeutic compounds for Alzheimer's disease, one would use a yeast system comprising at least amino acids 1-42 of the β-amyloid protein.

Likewise, in determining therapeutic compounds for scrapie, spongiform encephalopathy in a mammal, kuru, Creutzfeldt-Jakob disease, Gestmann-Strausser-Scheinker disease, or fatal familial insomnia, one would use a yeast system comprising the aggregate-forming domain of PrP. In preferred embodiments, the mammalian encephalopathy is bovine, feline, a mink, deer, elk, a mouse, a hamster, an ape, a monkey, or human.

Although many alternative forms of the PrP gene exist, the inventor contemplates that the expression in the yeast of a gene encoding the form linked to a specific disease is preferred for finding therapeutic agents for that disease. For example, for finding therapeutic agents for scrapie, it is preferred that proteins comprising aggregate forming domain of the goat or sheep PrP protein are expressed in the yeast. Of course, due to similarities between the PrP proteins, and even between the different types amyloid proteins, a therapeutic agent for one amyloidogenic disease may have therapeutic activity for one or more other amyloidogenic diseases.

As used herein "a" or "an" will be understood to mean one or more.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B and FIG. 1C. Specificity of circular dichroism spectral shifts with Hsp104 and Sup35. Right, predicted (--) and actual (-) spectra of mixed proteins. Left, individual spectra used to generate predicted spectra. (A) Sup35 in LSB1 (low salt buffer) with aldolase dolase or Hsp70. (B) Hsp104 and aldolase or IgM in LSB1. (C) Top, Hsp104 and Sup35 in LSB1. Bottom, Hsp104 and Sup35 in HSB (high salt buffer). Data, buffer spectra subtracted, are presented in millidegrees because the possibility of proteins partitioning out of solution invalidates molar ellipticity calculations. Hsp104, Hsp70, aldolase, or the buffer in which they were prepared was directly added to Sup35 at a ~1:2.5 gram-weight ratio. Reactions were incubated for 1 hr with 1 mM ATP at 37° C. and spectra were then recorded at 25° C.

FIG. 2A, FIG. 2B, FIG. 2C and FIG. 2D. Specificity of circular dichroism spectral shifts with Hsp104 and rPrP. Predicted (--), actual (-) and individual spectra as in FIG. 1. rPrP was prepared and folded into either β sheet or α helical forms. (A) Hsp104 and rPrPβ; (B) GroEL and rPrPβ; (C) Aldolase and rPrPβ; (D) Hsp104 and rPrPα. Proteins and rPrP were mixed (each at 0.5 mg/ml) with each other in LSB2. Reactions were incubated at 37° C. for 1 hr, diluted 5-fold with cold water, and spectra were measured at 12° C.

Figure 3:
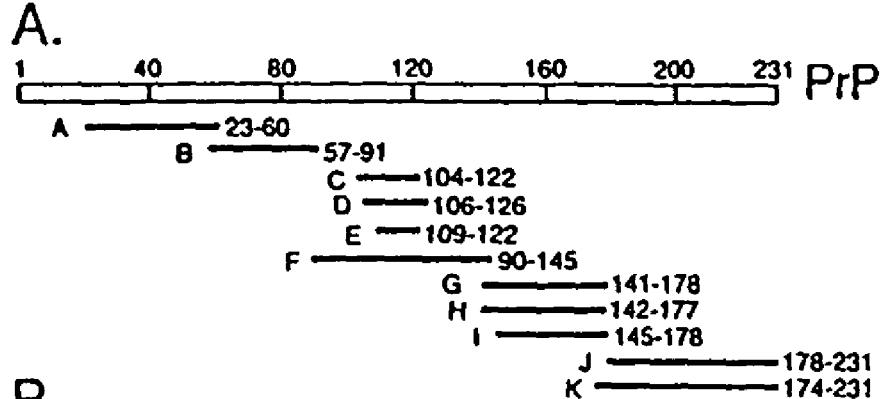
Figure 3:
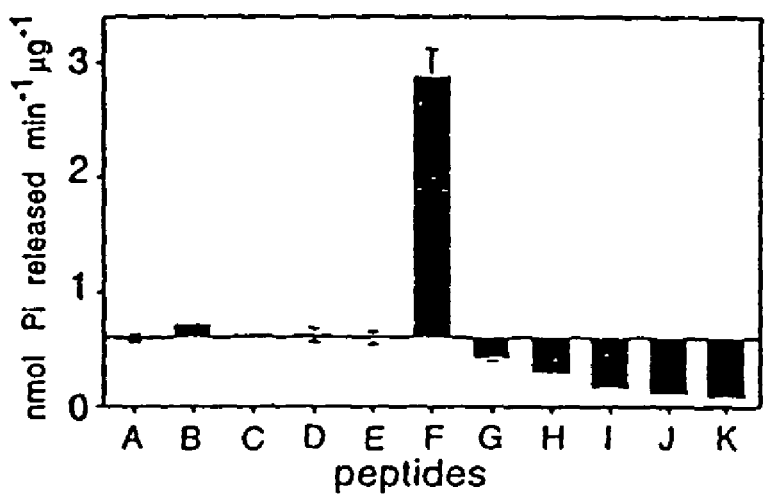

FIG. 3A and FIG. 3B. Effects of mixing PrP peptides with Hsp104. (A) Location of peptides used in this study. Peptides prepared as in (Zhang et al., 1995) were derived from the hamster PrP sequence except for peptide K, derived from mouse PrP. (B) Effects of PrP peptides on the ATPase activity of Hsp104. Bars extend from the value obtained for Hsp104 without added peptide.

FIG. 4A, FIG. 4B, FIG. 4C and FIG. 4D. Specificity of circular dichroism spectral shifts with different PrP peptides. Predicted (--), actual (-) and individual spectra as in FIG. 1. Reactions were performed as in FIG. 2 except that the buffer used was 20 mM Tris, 10 mM MgSO$_4$, 50 mM KCl, 1.25 mM ATP at pH 7.5 to approximate ATPase assay conditions.

FIG. 5A, FIG. 5B, FIG. 5C, FIG. 5D, FIG. 5E and FIG. 5F. Effects of chaperones on cell-free conversion of $^{35}$S-PrP$^C$ to its protease-resistant form.

FIG. 5A. Conversions (as percent of total $^{35}$S-PrP$^C$) obtained after 24 hours either with PrP$^{Sc}$ or without PrP$^{Sc}$ (100 ng), but with the indicated chaperones (each at 5 μM, with 5 mM ATP), using the standard assay described in methods. In indicated reaction (second from left), PrP$^{Sc}$ was partially-denatured with guanidinium hydrochloride (GdnHCl). Identical results were obtained, over a broad range of chaperone concentrations, with or without ATP.

FIG. 5B. Conversions performed as in A, with the addition of untreated PrP$^{Sc}$. Mean values are from 3-6 studies, with standard errors. Buffers for storing various chaperones differed slightly in salt and glycerol content, but none affected conversion.

FIG. 5C. Concentration-dependent effects of chaperones in promoting conversion with untreated PrP$^{Sc}$. Other Hsps tested as in FIG. 5A.

FIG. 5D. SDS-PAGE phosphorimage of $^{35}$S-PrP$^C$ products from representative conversion reactions obtained with 3 ng $^{35}$S-PrP$^C$ and increasing amounts of PrP$^{Sc}$ (3-1000 ng). One tenth of each reaction was left untreated (–PK); the remainder was digested with proteinase K (+PK). GroEL and GroES were at 1 μM. When indicated, PrP$^{Sc}$ was partially-denatured with GdnHCl. PrP$^{Sc}$ fold represents the ratio of PrP$^{Sc}$:$^{35}$S-PrP$^C$ in the reaction.

FIG. 5E. ATP dependence of GroEL-mediated conversions. SDS-PAGE phosphorimages of representative conversion reactions obtained with untreated PrP$^{Sc}$ and GroEL (WT and mutant D87K), with or without ATP. Both proteinase K-treated (+PK; bottom) and untreated samples (–PK, one-fifth sample; top) are shown.

FIG. 5F. $^{35}$S-PrP$^{GPI-}$ conversions with or without chaperones. Reactions contained either untreated PrP$^{Sc}$ or GdnHCl-treated PrP$^{Sc}$, and a variant PrP missing the GPI anchor, $^{35}$S-PrP$^{GPI-}$. $^{35}$S-PrP$^{GPI-}$ and $^{35}$S-PrP$^C$ preparations are compared (right panel): UG unglycosylated, MG monoglycosylated, and DG diglycosylated PrP species as indicated.

FIG. 6A, FIG. 6B and FIG. 6C. Time course of conversion with or without chaperone.

FIG. 6A. Appearance of PrP-res at 2, 6, 24, and 48 hours, in reactions treated with proteinase K, analyzed by quantitative phosphorimaging of SDS-PAGE. Mean values from three independent measurements, with standard errors.

FIG. 6B. Pelletable $^{35}$S-PrP determined by quantitative phosphorimaging of SDS-PAGE. At the indicated times, $^{35}$S-PrP reaction products were centrifuged at 15,000×g for 30 minutes at 22° C. After separating the supernatant fraction (S), the pelletable fraction (P) was resuspended in conversion buffer, and both fractions were prepared for SDS-PAGE. Mean values from three independent studies, with standard errors.

FIG. 6C. Protease-resistant $^{35}$S-PrP in pellet (P) and supernatant (S) fractions quantified from SDS-PAGE phosphorimages of 24 hour reactions. Average of two independent studies.

FIG. 7A, FIG. 7B, FIG. 7C and FIG. 7D. Combined effects of chaperones and partially-denatured PrP$^{Sc}$ on conversion.

Figure 7A:
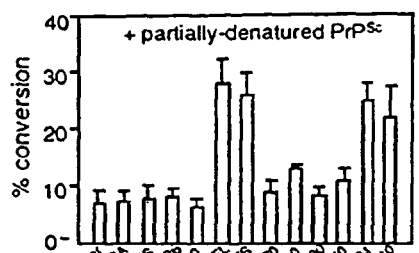

FIG. 7A. Conversions obtained with partially-denatured PrP$^{Sc}$ (4M urea pre-treatment) with buffer alone, or with the indicated chaperones and control proteins (each at 5 μM). Mean values from 3-6 independent measurements, with standard errors.

Figure 7B:
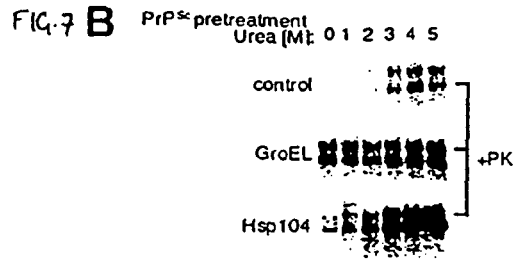

FIG. 7B. SDS-PAGE phosphorimage of representative conversion reactions obtained with untreated PrP$^{Sc}$ (0) or PrP$^{Sc}$ partially denatured in the presence of increasing urea concentrations (1-5 M), with or without chaperone (Hsp104 or GroEL, 3 μM). Only proteinase K-treated (+PK) samples are shown.

Figure 7C:
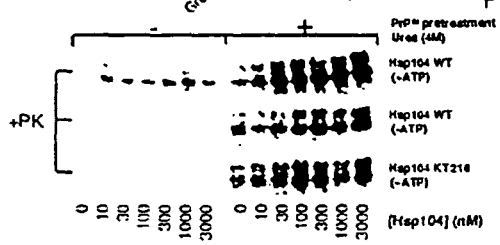

FIG. 7C. SDS-PAGE phosphorimage of representative conversion reactions obtained with Hsp104 (WT or mutant KT218), with or without ATP, and untreated or partially-denatured PrP$^{Sc}$ (4M urea pre-treatment). Only proteinase K-treated samples (+PK) are shown.

Figure 7D:

FIG. 7D. SDS-PAGE phosphorimage of representative conversion reactions obtained with partially-denatured PrP$^{Sc}$ (4M urea pre-treatment), with or without ATP, and with or without GroEL (WT or mutant D87K). Both proteinase K-treated (+PK; bottom) and untreated samples (–PK, one-fifth sample; top) are shown.

Figure 8:
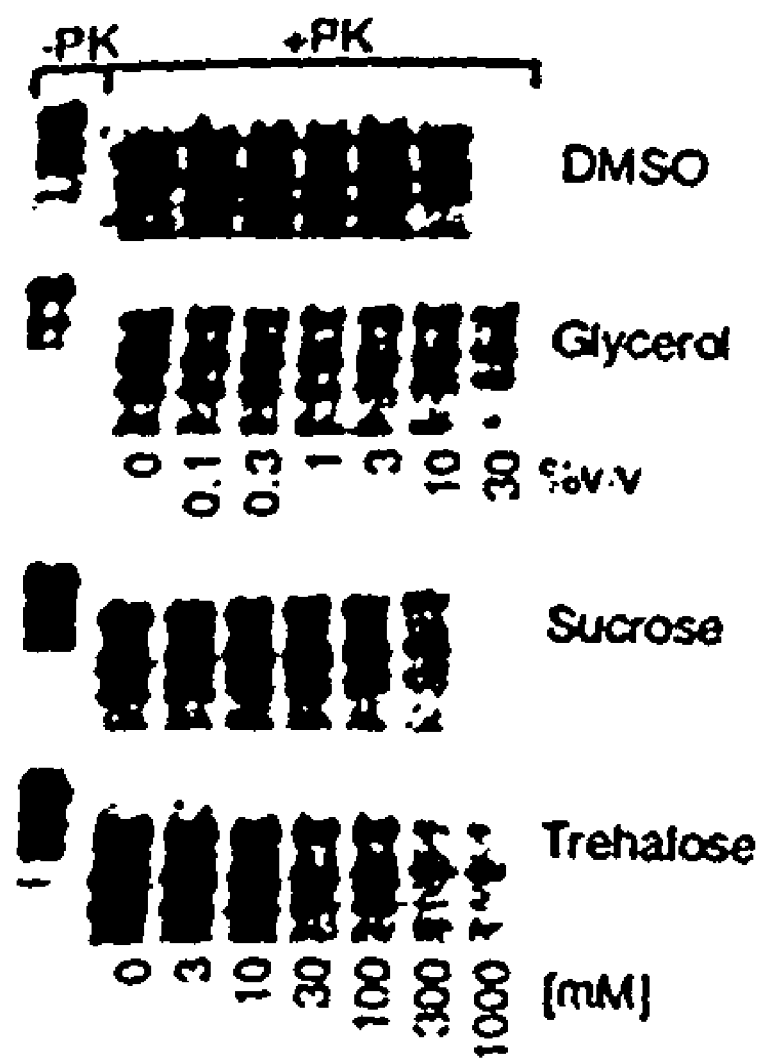

FIG. 8. Conversion of $^{35}$S-PrP$^C$ in the presence of chemical chaperones. SDS-PAGE phosphorimages of representative conversion reactions obtained with partially-denatured PrP$^{Sc}$ (4M urea pre-treatment) in the presence of increasing concentrations of DMSO, glycerol, sucrose, or trehalose.

4.0 DESCRIPTION OF ILLUSTRATIVE EMBODIMENTS

The invention demonstrates that yeast cells provide a system in which the folding of amyloidogenic proteins from diverse organisms is subject to manipulation. The most immediate application is the use of yeast cells to screen for reagents that affect amyloid formation, a process that is integral to several devastating human diseases. Screening for agents that affect these disease factors is very expensive and time consuming in animal models and cultured cells. Yeast will provide a rapid first screening system to quickly and cheaply identify reagents that affect the folding and aggregation properties of the target protein. These can then be screened by conventional methods to determine which are therapeutically applicable.

The inventor has found that Hsp104 controls the behavior of a factor that alters a particular physiological property of yeast cells in a heritable way. This change in physiology was shown to be associated with a heritable change in the aggregation state of a particular protein, Sup35, that is controlled by genetic manipulation of Hsp104. Subsequently, the inventor demonstrated that Sup35 has a very unusual biochemical property that it shares with certain human disease proteins. Specifically it forms amyloid fibers that stain with the dye Congo Red and shows apple green birefringence. Staining with this dye is a common diagnosis for human amyloid diseases (Glover et al., 1997; incorporated herein by reference).

The present invention is based, in part, on the inventor's discovery that, in a purified system in vitro, Hsp104 affects the folding state of the yeast amyloidogenic protein Sup35. Moreover, it also affects the folding state of a mammalian amyloidogenic protein, the prion protein known as PrP. The yeast protein was also shown to interact in a highly specific manner with another mammalian amyloid protein, β-amyloid peptide 1-42 (Alzheimer's disease peptide). The inventor has established that the folding state of the mammalian PrP protein, when expressed in yeast, depends upon the same type of manipulations that the folding of the yeast amyloid Sup35 depends upon. This establishes that yeast provides a surprisingly advantageous and widely applicable system for testing factors that affect the folding and amyloidogenic properties of mammalian disease proteins (Schirmer and Lindquist, 1997; DebBurman et al., 1997).

4.1 Methods of Screening and Selecting Amyloid Formation

The inventor contemplates that the formation of amyloid fibers may be detected by a number of mechanisms. In some embodiments, the aggregation may be detected by its ability to bind Congo Red and show apple green birefringence under polarized light (Baker et al., 1994; Guiroy et al., 1993; Gasset et al., 1992; Tashima et al., 1986; Bockman et al., 1985; Bendheim et al., 1984; Prusiner et al., 1983). However, in other embodiments, the aggregation is detected indirectly. For example, in embodiments comprising the Sup35 aggregation domain (N-terminal domain), the physiologically important C-terminal domain may be sequestered in the cell by the addition of the endogenous Sup35 protein into the aggregation, causing a change in phenotype of the cell. Thus, aggregation may be detected by the presence of the [PSI+] phenotype in the yeast cells. Depending upon how much of the Sup35 comprising protein is expressed and aggregated in the yeast, this phenotype is characterized by an increase in nonsense suppression, lesser aggregation, or cell death, higher aggregation.

Chernoff et al. (1995) used a color test for the [PSI+] phenotype. In this test, a adel-14 strain was used. In this strain, the adel-14 nonsense mutation is suppressed in the presence of the [PSI+] phenotype. This leads to white colored colonies. In the absence of the [PSI+] phenotype, this strain has a red color. This test provides a screen for the [PSI+] phenotype. Therefore, the ability of conditions or compositions to affect the [PSI+] phenotype may be detected by their ability to affect a color change in this [PSI+]/adel-14 strain.

In some preferred embodiments, the [PSI+] phenotype kills the yeast cell. Such cells are particularly useful in screening for the [PSI+] phenotype. For example, yeast expressing a chimeric protein comprising the β-amyloid peptide (1-42) and the Sup35 C-terminal domain have a [PSI+] phenotype that leads to cell death. The inventor contemplates that such cells are an excellent system for screening candidate compounds for their ability to inhibit β-amyloid aggregation, because only yeast grown in the presence of compounds that inhibit or reverse the [PSI+] phenotype will survive.

The inventor has shown that chimeric proteins comprising an aggregate prone domain have prion properties. For example, in a yeast expressing a chimeric protein comprising the N-terminal domain of Sup35 and GFP, the GFP was shown to aggregate. This same result was seen in a yeast strain expressing a chimeric protein comprising the N-terminal domain of Sup35 and GFP but that lacked expression of the N-terminal domain of the endogenous Sup35. This shows the aggregation of the chimeric protein was independent of the endogenous protein comprising the aggregate prone domain. Furthermore, chimeric proteins comprising GFP may be particularly useful in methods of screening agents that prevent aggregation, as the fluorescence pattern GFP is quickly and easily screened.

The inventor contemplates that, because chimeric proteins comprising an aggregate prone domain take on prion-like properties in yeast, such proteins are useful in developing screens or selections for the presence of aggregation. When a chimeric protein comprising an aggregate prone domain, such as the N-terminal domain of Sup35, and another polypeptide, such as luciferase or the glucocorticoid receptor, is expressed in yeast under conditions that lead to aggregation, aggregation of the chimeric protein leads to changes in the activities of the other polypeptide. Therefore, in yeast cells comprising the Sup35 aggregate prone domain and luciferase, the presence of aggregation can be detected by the loss of luciferase activity in the cells. In other preferred embodiments, the chimeric protein comprises an aggregate prone domain and a drug-resistance marker. In such embodiments, aggregation leads to antibiotic sensitivity.

4.2 Amyloid Diseases

In an important embodiment, the present invention is a screen for compounds that are therapeutic for amyloid diseases. The inventors contemplate that, by using polypeptides comprising the etiological agent of the amyloid disease, the methods of the present invention may be used to find therapeutic compounds for essentially any amyloid disease. A number of amyloid diseases occur in mammals and are discussed herein.

A number of neurodegenerative diseases in mammals have been linked to the aggregation of the product of the PrP gene (prion protein). Such diseases include scrapie in sheep and goats, mad cow disease (bovine spongiform encephalopathy), transmissible mink encephalopathy, chronic wating disease in captive mule deer and elk, feline spongiform encephalopathy, and prion diseases of other animals including mice, hamsters, nyala, greater kudu, eland, gembok, arabian oryx. Of course, prion diseases are also seen in apes, monkeys, and humans.

In humans, as in many animals, prion diseases can be sporadic, inherited, or may be brought on by inoculation with infectious prion particles. Common names of prion diseases in humans are kuru, Creutzfeld-Jakob disease (CJD), Gerstmann-Straussler-Scheinker (GSS), and fatal familial insomnia (FFI). The classification of human prion diseases is based on clinical and neuropathological findings (Prusiner, 1996; incorporated herein by reference).

Prion diseases resulting from the horizontal transmission of infectious prions are iatrogenic CJD and kuru. Inherited forms GSS, fanilial CJD, and FFI have all been associated with oneor more mutations in the protein coding region of the PrP gene (Bertoni et al., 1992; Dlouhy et al., 1992; Doh-ura et al., 1989; Gabizon et al., 1993; Goldfarb et al., 1990; Goldfarb et al., 1991; Goldfarb et al., 1992; Goldgaber et al., 1989; Hsiao et al., 1989; Kitamoto et al., 1993a; Kitamoto et al., 1993b; Medori et al., 1992; Petersen et al., 1992; Poulter et al., 1992). Sporadic forms of prion disease in humans comprise most cases of CJD and some cases of GSS (Masters et al., 1978).

Regardless of the origin of the prion diseases, all have been associated with abnormal folding of the cellular protein $PrP^c$ into a protease resistant form, $Pa^{sc}$, that aggregates (Oesch et al., 1985; Bolton et al., 1982; McKinley et al., 1982; Bolton et al., 1984; Prusiner et al., 1984; Bolton et al., 1987).

Another amyloid disease in humans is Alzheimer's disease (AD). One of the key events in AD is the deposition of amyloid as insoluble fibrous masses (amyloidogenesis) resulting in extracellularneuritic plaques and deposits around the walls of cerebral blood vessels (WO 96/39834; incorporated herein by reference). The main component of amyloid is a 4.1-4.3 kDa peptide, called β-amyloid, that is part of a much longer amyloid precursor protein APP (Muller-Hill and Beyreuther, 1989). Peptides containing the sequence 1-40 or 1-42 of β-amyloid and shorter derivatives can form amyloid-like fibrils in the absence of other protein (Pike et al., 1993).

The inventors have shown that proteins comprising PrP and β-amyloid polypeptides are capable of forming aggregates in a yeast based system. Thus, this system provides a mechanism of testing compounds for their ability to inhibit the aggregation of these polypeptides in an inducible, yeast-based system. Such compounds may be used as amyloid disease therapeutic compounds.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Interactions of the Chaperone Hsp104 with Yeast Sup35 and Mammalian PrP

A critical missing link in the "protein-only" hypothesis for [PSI+] inheritance is any evidence that Hsp104 actually interacts directly with Sup35. Indeed, little is known about the interaction of Hsp104 with any substrate, as the heat-denatured aggregates that constitute its other likely in vivo substrates are inherently difficult to study. Here the inventor provides evidence for a highly specific interaction in vitro between Hsp104 and Sup35. This interaction produces a change in protein structure and inhibits the ATPase activity of Hsp104. The inventor also reports that Hsp104 interacts in a remarkably similar way with mammalian PrP, the protein determinant of the neurodegenerative "prion" diseases (Prusiner, 1996; Caughey and Chesebro, 1997), and with β-amyloid peptide (Glenner and Wong, 1984).

5.1.1 Materials and Methods 5.1.1.1 Protein and Peptide Preparation

Hsp104 (prepared as in 12), Hsp70 (obtained from J. Glover), aldolase (Pharmacia), and IgM (Rockland) were stored in 20 mM Tris pH 8.0, 2 mM EDTA, 1.4 mM β-mercaptoethanol, 5% glycerol, 1 mM 4-(2-aminoethyl)benzenesulfonyl fluoride (AEBSF). Sup35 and the fragment MN (purified as in 13) were dialyzed against HSB (high salt buffer, 20 mM HEPES pH 7.5, 10 mM $MgCl_2$, 140 mM KCl, 15 mM NaCl freshly supplemented with 5 mM β-mercaptoethanol and 1 mM AEBSF) to remove imidazole, and then dialyzed against either HSB or LSB (low salt buffer, 10 mM MES pH 6.5, 10 mM $MgSO_4$). Concentrations were determined by the Bradford assay with BSA (bovine serum albumin) as a standard. Concentrations of PrP (prepared and folded into either βsheet or α helical forms; Mehlhorn et al., 1996; Zhang et al., 1997), PrP peptides (as in 16), and β-amyloid (Sigma) were determined spectroscopically using calculated extinction coefficients.

5.1.1.2 ATPase Assays

PrP peptides (1 mM resuspended in $H_2O$ were assayed in 40 mM Tris pH 7.5, 175 mM NaCl, 5 mM $MgCl_2$, and 5 mM ATP in a 25 μl reaction volume containing 1 μg of Hsp104. Peptides A, G, H, and K were resuspended in dimethyl sulfoxide (DMSO) which was also added to controls containing Hsp104 alone. Effects of other proteins on Hsp104's ATPase activity were measured in LSB or HSB. Phosphate released (mean and standard deviation of at least 3 independent reactions) after 8 minutes at 37° C. was measured with Malachite Green (Lanzetta et al., 1979).

5.1.1.3 Spectropolarimetry

Hsp104, Hsp70, aldolase, IgM or storage buffer were added to Sup35 or rPrP in the buffers indicated. When aldolase and IgM were tested as substrates of Hsp104, they were first dialyzed against HSB and subsequently LSB, so that their treatment matched that of Sup35. In LSB Sup35 solutions were somewhat cloudy, suggesting some aggregation, but little or no protein precipitated to the bottom of cuvettes during analysis. Chaperones and control proteins were added to Sup35 at a ~1:2.5 gram-weight ratio (e.g. Sup35 at ~0.4 mg/ml and Hsp104 at 0.15 mg/ml). Reactions were incubated for 1 hr with 1 mM ATP at 37° C., and transferred to a 0.1 mm path-length cuvette. Spectra were recorded at 25° C. in a Jasco 715 spectropolarimeter (bandwidth 1.0 nm, response time 16 sec, speed 20 nm/min, step resolution 0.2 nm, accumulations 4).

Proteins and rPrP were mixed with each other (each at 0.5 mg/ml) or with the appropriate storage buffer in LSB2: 20 mM phosphate buffer pH 6.5, 10 mM $MgSO_4$, 1.25 mM ATP. PrP peptides were mixed with Hsp104 in 20 mM Tris buffer containing 10 mM $MgSO_4$, 50 mM KCl, and 1.25 mM ATP at pH 7.5 to approximate ATPase assay conditions. After 1 hr at 37° C., reactions were diluted 5-fold with cold water, and spectra were measured at 12° C. as above. (A larger spectral shift was observed with these conditions for peptide F, presumably because the structural changes obtained with this peptide are unstable at higher temperatures. Although temperature had little effect on the spectra obtained with other peptides or rPrP, for consistency, 12° C. was used for all.).

5.1.1.4 Congo Red Dye Binding Assays

Reaction conditions were as for CD studies with the addition of Congo red to a final concentration of 10 µM. After 30 min at 25° C., absorbances at 320, 477, and 540 nm were determined. Congo red dye binding was measured using the equation $[(OD_{540}/25,295)-(OD_{477}/46,306)]$ (Klunk et al., 1989).

5.1.2 Results 5.1.2.1 Circular dichroism of Hsp104 and Sup35 mixtures

Attempts to detect an interaction between Sup35 and Hsp104 by co-immunoprecipitation or by affinity chromatography with immobilized Hsp104 were unsuccessful suggesting that if Hsp104 interacts with Sup35, this interaction is weak, transient, or depends upon unique conditions, conformations, or cofactors. Since changes in the expression of Hsp104 lead to changes in the physical state of Sup35 in vivo, as an alternative mechanism for probing interactions between these proteins, the inventor discovered that changes in state could be detected by circular dichroism when purified Hsp104 and Sup35 were mixed in vitro. If two proteins do not interact, or if they interact without a substantial change in secondary structure, the CD spectrum of their mixture should equal that predicted from the simple addition of their individual spectra.

When either Sup35 or Hsp104 was mixed with any of several control proteins—aldolase, immunoglobulins (IgG and IgM), α-2 macroglobulin, apoferritin, and α-lactalbumin—observed spectra matched the predicted spectra (FIG. 1A and FIG. 1B). These control proteins encompass a wide variety of structural features, including proteins that are largely α-helical or β-sheet, monomeric or oligomeric, large or small. Furthermore, spectral shifts observed when another chaperone, Hsp70, was mixed with Sup35 were small (FIG. 1A).

In contrast, when Hsp104 and Sup35 were mixed, the observed spectrum differed dramatically from the predicted spectrum (FIG. 1C, top right). Thus, these two proteins interacted in a highly specific manner to produce a change in the physical state of one or both proteins. ATP is required for some Hsp104 functions (Parsell et al., 1994; Schirmer et al., 1996), but was not required for the change in CD spectrum with Sup35 and Hsp104. However, ATP markedly increased the rate at which this change occurred (Table 1).

The difference between the actual spectrum and the predicted spectrum at 225 nm for each timepoint is presented in millidegrees. In each of three separate studies, the spectral change in mixtures of Sup35 and Hsp104 proceeded more rapidly with ATP than without ATP, although the absolute rates varied, most likely due to differences in the Sup35 preparations.

The interaction between Hsp104 and Sup35 apparently depended upon the structural state of Sup35. When Sup35 was dialyzed against low salt buffer at pH 6.5 (LSB, FIG. 1C, top left, solid line) or a higher salt buffer at pH 7.5 (HSB, FIG. 1C, bottom left, solid line) a difference in the CD spectra indicated that the protein was in a different structural state. When Hsp104 was added, the actual CD spectrum deviated from the predicted spectrum only when Sup35 had been dialyzed in LSB (FIG. 1C, compare right panels). Mixtures of Sup35 and several control proteins showed no deviation from predicted spectra in LSB or HSB. Similarly, control proteins mixed with Hsp104 showed no spectral shifts in either buffer. Moreover, the CD spectrum of Hsp104 itself did not change with the buffer (FIG. 1C, left panels, dashed line).

5.1.2.2 Sup35 Aggregation

In vivo, the inheritance of [PSI+] is associated with the partitioning of Sup35 into aggregates, a change in state that requires Hsp104 (Paushkin et al., 1996; Patino et al., 1996; Chernoff et al., 1995). In vitro, Sup35 forms highly ordered, amyloid-like fibers after prolonged incubations in the absence of Hsp104 (Glover et al., 1997). In CD studies the proteins did not precipitate to the bottom of the cuvette or exhibit significant binding to the walls of the tube. However, the upward shift in the spectrum might be due, at least in part, to a partitioning of protein from solution while it remains in suspension (We and Chen, 1989).

To determine whether the interaction between Hsp104 and Sup35 detected by CD analysis in vitro is related to the biological interaction between the two proteins in vivo, the inventor investigated their association and changes in protein aggregation. Solutions containing mixtures of Sup35 and Hsp104 invariably scattered more light at 320 nm (typically ~30% more) than the simple sum of light scattering by each protein alone. An increase in Congo red dye binding was also detected by the characteristic spectral shift that occurs when this dye binds amyloid proteins (Klunk et al., 1989).

5.1.2.3 Effects of Sup35 on the ATPase Activity of Hsp104

When other members of the HSP100 (clp) family are incubated with substrates, the rate at which they hydrolyze ATP is increased (Maurizi et al., 1994; Hwang et al., 1988; Wawrzynow et al., 1995). Thus, changes in the ATPase activity of Hsp104 provide another method for detecting an interaction with Sup35. When assayed in HSB, in which no CD changes were observed, Sup35 weakly stimulated the ATPase activity of Hsp104 (Table 2). Surprisingly, in LSB, in which CD changes were observed, Sup35 strongly inhibited the ATPase activity of Hsp104.

TABLE 1

ATP affects rate of CD change

| Time, min | −ATP | +ATP |
|---|---|---|
| 0 | 2.9 | 2.2 |
| 3 | 7.9 | 15.2 |
| 6 | 9.9 | 17.2 |
| 10 | 10.9 | 18.2 |
| 15 | 11.8 | 18.8 |
| 20 | 12.4 | 19.2 |
| 30 | 13.3 | 19.8 |
| 72 | 16.2 | 21.9 |

TABLE 2

Effects of proteins and peptides on the ATPase activity of Hsp104

| | HSB | LSB |
|---|---|---|
| Hsp104 alone | 1.0 +/− 0.05 | 1.0 +/− 0.1 |
| Sup35 | 1.2 +/− 0.1 | 0.6 +/− 0.1 |
| N-term Sup35 | 1.2 +/− 0.1 | 0.7 +/− 0.1 |
| PrPβ | 1.2 +/− 0.1 | 0.6 +/− 0.05 |
| β-amyloid 1-42 | 0.8 +/− 0.05 | 0.3 +/− 0.05 |
| β-amyloid 1-40 | 1.1 +/− 0.05 | 0.5 +/− 0.1 |
| reverse amyloid 40-1 | 1.1 +/− 0.1 | 0.8 +/− 0.1 |

TABLE 2-continued

Effects of proteins and peptides on the ATPase activity of Hsp104

|  | HSB | LSB |
| --- | --- | --- |
| aldolase | 1.1 +/− 0.05 | 1.0 +/− 0.1 |
| BSA | 1.0 +/− 0.05 | 1.0 +/− 0.05 |
| apoferritin | 1.0 +/− 0.1 | 1.0 +/− 0.05 |
| IgM | 1.1 +/− 0.05 | 1.1 +/− 0.05 |

Hsp104 ATPase activity was measured in HSB or LSB1 and is presented as the activity of Hsp104 with protein divided by the activity of Hsp104 in buffer alone. Within individual studies very little variance was observed; however, even with the results from three different preparations of Sup35 averaged here, only ~10% variability was observed.

Previous studies identified the N-terminal domain of Sup35 as the essential "prion-determining" region (Ter-Avanesyan et al., 1993). This domain is also responsible for the formation of self-seeded amyloid fibrils by Sup35 in vitro. (Glover et al., 1997; King et al., 1997). The ATPase activity of Hsp104 was inhibited by this domain to an extent similar to that observed with Sup35 itself (Table 2).

5.1.2.4 Effects of Other Amyloids on the ATPase Activity of Hsp104

The expansion of the mammalian prion hypothesis to the yeast [PSI+] element was initially based upon genetic arguments. PrP and Sup35 are unrelated in sequence and in biological function (Wickner, 1994; Lindquist, 1997; Chernoff et al., 1995). Nonetheless, the capacity for both proteins to form amyloid-like aggregates (Glover et al., 1997; Prusiner et al., 1983; Gasset et al., 1992) suggests an underlying biochemical similarity between them. The inventor investigated whether this similarity would extend to shared molecular features in the two proteins that allow recognition by Hsp104.

The change in state of mammalian PrP associated with TSEs is characterized by increased β-sheet content and protease resistance in amino-acid segment 90 to 231 (Prusiner et al., 1982; Caughey et al. 1991). A recombinant hamster protein corresponding to this segment, in a β sheet-rich conformation, rPrPβ (Mehlhorn et al., 1996; Zhang et al., 1997), produced the same unexpected effect on the ATPase activity of Hsp104 as did Sup35 (Table 2).

The inventor also tested another amyloidogenic peptide, β-amyloid 1-42, a fragment often found in the neural plaques associated with Alzheimer's disease (Glenner and Wong, 1984). Again, the ATPase activity of Hsp104 was inhibited (Table 2). Less inhibition was observed with a less amyloidogenic derivative, β-amyloid 1-40, still less with a peptide containing the same amino acids in the reverse order, and no inhibition was observed with a wide variety of control proteins (Table 2). Thus, the unexpected inhibitory effects of these three amyloidogenic polypeptides on Hsp104's ATPase activity are specific and strongly suggest an underlying biochemical similarity between them.

5.1.2.5 Circular Dichroism of Hsp104 and PrP Mixtures

Figure 2B:
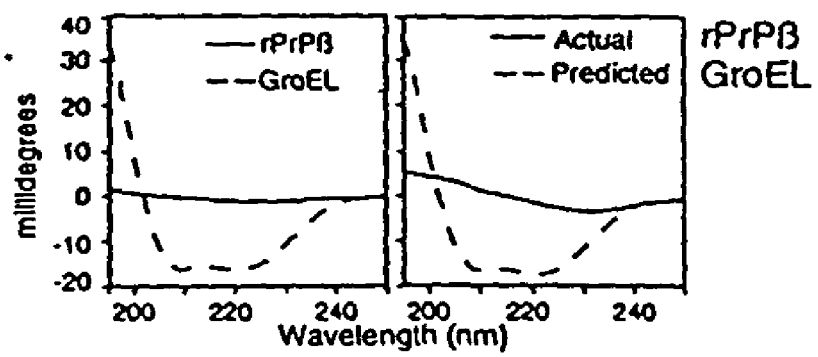
Figure 2C:
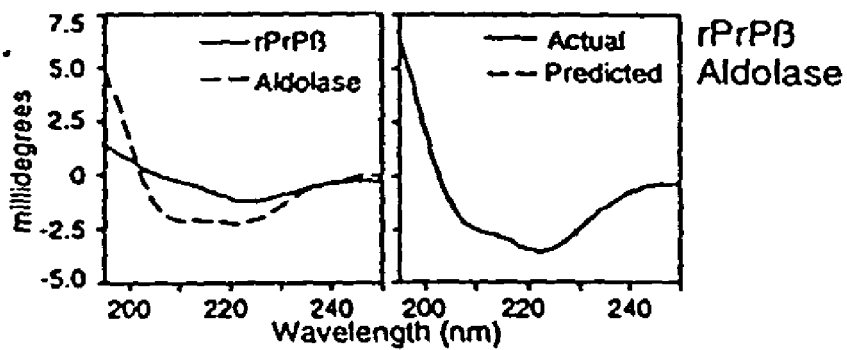

When Hsp104 was mixed with rPrPβ (Mehlhorn et al., 1996; Zhang et al., 1997), the CD spectrum of the solution differed dramatically from the spectrum predicted by the addition of individual spectra (FIG. 2A, right). This result was very reproducible in both degree and effect, with two different preparations of rPrP and two of Hsp104. When rPrPβ was mixed with several other chaperones, only GroEL (Hsp60) yielded a substantial spectral shift (FIG. 2B right). Other chaperones (Cdc37, Hsp90, Hsp70), as well as some non-chaperone proteins (apoferritin, β-galactosidase, α2-macroglobulin, and α-lactalbumin) yielded spectral shifts with PrP, but they were much smaller than those observed with Hsp104 and GroEL. Finally, when rPrPβ was mixed with BSA or aldolase (FIG. 2C right), predicted and actual spectra were virtually identical.

Figure 2D:
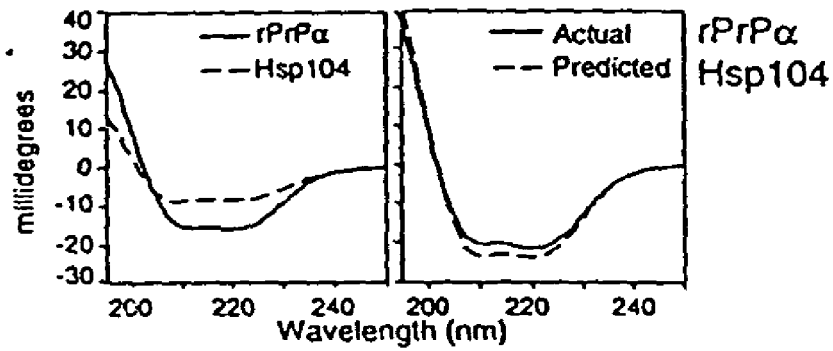

As with Sup35, the interaction between Hsp104 and rPrP depended upon the structural state of rPrP. When rPrP was pre-incubated under conditions (Mehlhorn et al. 1996; Zhang et al., 1997) that promote an α-helical conformation (rPrPα) rather than a β sheet-rich conformation (rPrPβ), and mixed with Hsp104, the actual spectrum matched the predicted spectrum (FIG. 2D, right). The α-helical and β sheet-rich forms of rPrP, once acquired, were stable after transfer to the same buffer. Since they were in the same buffer when mixed with Hsp104, the different results obtained with rPrPα and rPrPβ can be attributed to an effect of substrate structure on interaction with Hsp104, rather than to an effect of buffer.

5.1.2.6 Correlation Between Structural Transitions and ATPase Inhibition with PrP Peptides Since for both Sup35 and PrP, the inhibition of Hsp104's ATPase activity occurred under the same conditions where a spectral shift occurred, the inventor postulated that these amyloidogenic proteins might inhibit the ATPase activity of Hsp104 by coupling it to a major change in structure. To investigate this possibility further, the inventor took advantage of various PrP peptide derivatives (FIG. 3A) and the structural transitions of both PrP and these derivatives (Mehlhorn et al. 1996; Zhang et al., 1997; Zhang et al., 1995; Gasset et al., 1992; Nguyen et al., 1995). Several peptides from the amino-terminal region had little or no effect on the ATPase activity of Hsp104 (FIG. 3B, peptides A and B); a peptide corresponding to amino acids 90-145 strongly stimulated ATP hydrolysis by Hsp104 (FIG. 3B, peptide F); several peptides derived from the carboxy-terminus inhibited it (FIG. 3B, peptides G to K).

Peptides with different effects on the ATPase activity of Hsp104 were then tested for spectral shifts in the presence of Hsp104. When peptide β was mixed with Hsp104, the CD spectrum was equivalent to that predicted from the addition of the individual spectra (FIG. 4A). The actual and predicted spectra of Hsp104 and peptide F were not identical, but the deviation was small (FIG. 4B). In contrast, the spectra obtained from mixing Hsp104 with the carboxyl-terminal peptides G and J were very different from the predicted spectra (FIG. 4C and FIG. 4D). Thus, the PrP peptides that inhibited the ATPase activity of Hsp104 yielded the strongest spectral shift.

5.1.3 Discussion

The dependence of [PSI+] on the protein chaperone Hsp104 provides one of the strongest genetic arguments that the inheritance of a phenotypic trait can be due to the inheritance of a change in protein conformation, in this case, the conformation of Sup35 (Paushkin et al., 1996; Patino et al., 1996; Chernoff et al., 1995). The validity of this argument rests on two assumptions, 1) that Hsp104 and Sup35 interact directly, and 2) that this interaction influences the physical state of Sup35. Here the inventor provides evidence in support of both. Remarkably, very similar results were obtained with PrP, the mammalian protein whose altered conformation is thought to propagate the transmissible spongiform encephalopathies (Prusiner, 1996; Caughey and Chesebro, 1997). β-amyloid, the peptide whose deposition in amyloids is thought to contribute to Alzheimer's disease (Glenner and Wong, 1984) also interacted with Hsp104 in a similar manner. These findings reveal an underlying biochemical similarity between these otherwise unrelated proteins.

Circular dichroism studies provided one line of evidence for the direct interaction of Hsp104 with Sup35 and with PrP. The actual spectra observed when Hsp104 is mixed with either of these proteins is different from the spectra predicted by the simple addition of their individual spectra. These spectral shifts are highly specific. When control proteins, encompassing a wide variety of structural features, are mixed with Hsp104, actual spectra match the predicted spectra. Further, when Sup35 or rPrPβ are mixed with control proteins (including other chaperones) spectral deviations are relatively small, or undetectable (except in the case of rPrPβ and GroEL). Finally, the interactions of Hsp104 with Sup35 and PrP themselves appear to depend upon the initial structural states of Sup35 and PrP.

Currently, producing different structural states of Sup35 depends upon using different buffers and, although these buffers did not influence Hsp104's CD spectum, they might influence Hsp104's interaction with Sup35. However, in the case of rPrP distinct conformational states, once established, are stable on transfer to the same buffer (Mehlhorn et al. 1996; Zhang et al., 1997). A large spectral shift occurs with rPrPβ, a β sheet-rich, multimeric conformation (Zhang et al., 1997) thought to be associated with TSE diseases, but not with rPrPα, an α helix-rich, monomeric conformation thought to mimic the normal cellular form.

The ability of both Sup35 and PrP to inhibit the ATPase activity of Hsp104 provides independent evidence for an interaction between these proteins. The same specificity was observed as with CD: 1) control proteins do not inhibit the ATPase activity of Hsp104, 2) Sup35 inhibits it under the conditions that lead to a change in CD spectrum, but not under the conditions where no change in CD spectrum occurred, and 3) rPrPβ also inhibited it under the conditions that lead to a change in the CD spectrum. Studies with a series of peptides spanning the PrP sequence provide another link between the Hsp104::substrate interactions that lead to structural transitions and those that inhibit ATPase activity. The strongest inhibition in Hsp104's ATPase activity occurred with the peptides that produced the strongest CD shifts.

The inhibition of Hsp104's ATPase activity was itself surprising. Interactions between other HSP100 proteins and their substrates generally stimulate the chaperone's ATPase activity (Maurizi et al., 1994; Hwang et al., 1988; Wawrzynow et al., 1995). At least some of these interactions, however, seem to involve less dramatic structural transitions (Schirmer et al., 1996). For example, ClpA (an $E.$ $coli$ relative of Hsp104) converts the RepA protein from diers to monomers (Wickner et al., 1994). Both ClpA and Hsp104 are hexameric proteins with multiple ATP binding sites and, presumably, multiple substrate binding sites. Perhaps the structural transitions of more complex, amyloidogenic substrates involve more coupled or "concerted" work from the chaperone and this inhibits its free-running ATPase activity.

It is striking that this β-amyloid peptide also inhibited the ATPase activity of Hsp104. β-amyloid, Sup35, and PrP differ in size and biological function and have unrelated sequences (except for weak homology in a few oligopeptide repeats of Sup35 and PrP). Yet, all share the capacity to assemble into amyloid-like aggregates (Glenner and Wong, 1984; Glover et al., 1997; Prusiner et al., 1983). The [PSI+] genetic trait is linked to the aggregation of Sup35; the pathologies of TSEs and Alzheimer's disease are generally associated with the aggregation of PrP and β-amyloid respectively (Prusiner, 1996; Caughey and Chesebro, 1997; Glenner and Wong, 1984). Presumably, it is the shared capacity for such conformational transitions that leads to recognition by Hsp104.

5.2 Example 2

Chaperone-Supervised Conversion of Prion Protein to its Protease-Resistant-Form

Shown in this example is an assessment of whether or not molecular chaperones, whose known functions are to alter the conformational states of proteins (Hartl, 1996; Buchner, 1996; Parsell and Lindquist, 1993), regulate the conversion of $PrP^{C}$ to $PrP^{Sc}$. To test for chaperone involvement, the inventor used a cell-free assay, wherein metabolically-labeled $^{35}S$-$PrP^{C}$, purified from cultured cells in an acid-treated state, is converted to a conformational state characteristic of $PrP^{Sc}$ (Kocisko et al., 1994; Caughey et al., 1995). In this altered state, PrP is aggregated and a specific portion of the molecule is highly resistant to proteolysis.

This simple in vitro conversion reaction faithfully recapitulates several salient TSE features. First, like experimental TSEs, in vitro conversion of $PrP^{C}$ to its protease-resistant form requires pre-existing $PrP^{Sc}$(Kocisko et al., 1994; Caughey et al., 1995; Bessen et al., 1995; Kocisko et al., 1995). Secondly, strain-specific $PrP^{Sc}$ protease digestion properties, specifically those associated with two mink TSE strains—hyper and drowsy, were precisely propagated from $PrP^{Sc}$ to radiolabeled $PrP^{C}$ in this assay (Bessen et al., 1995). Thirdly, the known in vivo barriers to transmitting TSEs between different species were reflected well in the efficiencies of in vitro conversion (Kocisko et al., 1995; Raymond et al., 1997). Lastly, this cell-free assay modeled accurately another in vivo TSE barrier, based on genetic polymorphisms in PrP, which render sheep either highly susceptible, moderately susceptible, or resistant to scrapie (Bossers et al., 1997).

Together, these studies provide substantial evidence that in vitro converted, protease-resistant PrP is either authentic $PrP^{Sc}$ or has a very similar conformation. The in vitro converted material is operationally referred to herein as protease-resistant PrP (PrP-res).

Here, the inventor provides the first evidence that molecular chaperones can regulate conformational transitions in PrP. Two protein chaperones, GroEL and Hsp104, promoted in vitro conversion, in contrast, the chemical chaperones, sucrose, trehalose, and DMSO inhibited it. Importantly, the inventor's results with chaperones demonstrate that in vitro converted PrP-res is a bonafide conformationally-altered PrP molecule. Chaperones provide new understanding of the nature of PrP intermediates involved in PrP conversion, and provide evidence that the conversion process has two steps. The ability of chaperone-like molecules to supervise $PrP^{Sc}$ formation in TSEs in vivo means that these molecules represent important clinical targets to combat this dreaded disease.

5.2.1 Materials and Methods 5.2.1.1 Chaperone Proteins

Yeast Hsp40 (Ydj1), Hsp70 (ssa1/ssa2), and Hsp104 (WT and mutant) were purified as previously described (Cyr et al., 1992; Zeigelhoffer et al., 1995; Parsell et al., 1993) and were obtained from J. R. Glover and Y. Kimura. Bacterial GroES and GroEL (WT and mutant) were obtained by A. L. Horwich. Hsp26 was obtained from T. Suzuki and E. Vierling, and Yeast Hsp90 was obtained by J. Buchner.

5.2.1.2 Chaperone Folding Assays

Hsp104 promoted the refolding of kinetically-trapped denatured luciferase, but only when Hsp40, Hsp70 and ATP were also present (J. R. Glover and S. Lindquist, manuscript in preparation). The function of other chaperones were assessed using previously published procedures. GroEL and GroES activities were measured by the refolding of denatured rhodanese (Mendosa et al., 1991); Hsp90 suppressed the aggregation of β-galactosidase (Freeman and Morimoto, 1996); Hsp26 activity was measured by the suppression of aggregation of malate dehydrogenase (Lee et al., 1995).

5.1.1.3 PrP Purification $PrP^{Sc}$ was purified from hamsters infected with 263K strain of scrapie as previously described (Kocisko et al., 1994). Hamster $^{35}S\text{-}PrP^{C}$ and $^{35}S\text{-}PrP^{-GPI-}$ proteins were purified from cultured cells by a procedure described in B. Caughey et al., (1996) (Caughey et al. 1995), except that radiolabeled proteins were eluted with 0.1M acetic acid at 22° C. for 30 minutes and stored at 4° C. before use. To obtain non-glycosylated $^{35}S\text{-}PrP^{C}$, cultured cells were pre-incubated and $^{35}S$-labeled in the presence of 2 μg/ml tunicamycin (Boehringer-Mannheim), an inhibitor of glycosylation (Caughey et al., 1995).

5.2.1.4 Cell-Free PrP Conversion

Unless otherwise stated, all reactions were performed using the same modification of a published procedure (Caughey et al., 1995). $^{35}S\text{-}PrP^{C}$ (20,000 cpm ~3 ng) denatured in 0.1M acetic acid was diluted into 1× conversion buffer (CB: 50 mM sodium citrate-HCl, pH 6.0, supplemented with 1% N-lauryl sarkosine). $PrP^{Sc}$ (100 ng) was incubated with $^{35}S\text{-}PrP^{C}$ (20 μl volume) at 37° C. for 24 hours. When indicated, $PrP^{Sc}$ was pretreated for one hour with either 2M GdnHCl at 37° C. or 4M urea at 22° C.; in conversion reactions, GdnHCl and urea were present at 0.2M and 0.4M respectively. In chaperone-mediated conversions, chaperones (1 μM, unless otherwise stated) were added to CB prior to the addition of $^{35}S\text{-}PrP^{C}$ and $PrP^{Sc}$. Reactions with chaperones contained 10 mM $MgCl_2$, 1.5 mM NaCl, and 140 mM KCl, and unless otherwise stated, 5 mM ATP. All reactions with ATP included an ATP regenerating system containing 20 mM phosphocreatine and 10 μg/ml creatine phosphokinase. These supplements did not affect PrP conversion.

For each reaction, one-tenth to one-fifth of the sample was left untreated for determination of percent conversion of $^{35}S\text{-}PrP^{C}$ to PrP-res (Caughey et al., 1995). The remainder was digested with proteinase K (PK; 80 μg/ml) for 1 hour at 37° C., and both PK-untreated and PK-treated samples were prepared for SDS-PAGE (Caughey et al., 1995). $^{35}S$-PrP products were visualized in dried gels by phosphorimaging and quantified with ImageQuant software (Molecular Dynamics).

5.2.2 Results 5.2.2.1 Chaperones alone do not convert $PrP^{C}$ to PrP-res

The inventor first examined the ability of major cellular chaperones GroES (Hsp10), Hsp26, Hsp40, GroEL (Hsp60), Hsp70, Hsp90, and Hsp104, to promote $^{35}S\text{-}PrP^{C}$ conversion in the absence of $PrP^{Sc}$. These chaperones were chosen because they employ different mechanisms to affect the conformation and physical state of other proteins (Hartl, 1996; Buchner, 1996; Parsell and Lindquist, 1993). In separate studies, these same chaperone preparations functioned appropriately in a variety of protein folding assays. Yet, over a broad range of concentrations, alone and in various combinations, with (FIG. 5A) or without ATP, none of these chaperones promoted the conversion of $PrP^{C}$ to PrP-res, in the absence of $PrP^{Sc}$. This observation strongly underscores the importance of pre-existing $PrP^{Sc}$ in the conversion of $PrP^{C}$.

5.2.2.2 GroEL Promotes Conversion in Reactions Nucleated with Untreated $PrP^{Sc}$ Next, the inventor determined whether chaperones influenced $^{35}S\text{-}PrP^{C}$ conversion in the presence of $PrP^{Sc}$. To date, efficient in vitro conversion of $PrP^{C}$ to PrP-res has usually required partial chemical denaturation of $PrP^{Sc}$(left bars, FIG. 5A; Edenhofer et al., 1996; Freeman and Morimoto, 1996). Untreated and completely denatured $PrP^{Sc}$(6M GdnHCl pretreatment) have little (FIG. 5D) and no converting ability respectively (Kocisko et al., 1994; Caughey et al., 1995). The inventor first asked if chaperones influenced conversion with PrP-res that was not subjected to partial denaturation. Several chaperones produced reproducible, but very small increases in conversion (FIG. 5B and FIG. 5D). One, however, facilitated conversion at a high level (FIG. 5A and FIG. 5B). With GroEL, typically 25-30%, and occasionally 50-100%, of $^{35}S\text{-}PrP^{C}$ converted.

Notably GroEL not only reduced by 10-fold the quantity of $PrP^{Sc}$ required for detectable conversion, but also increased by more than 10-fold the maximal levels of conversion attained, compared to reactions nucleated with the same preparation of untreated $PrP^{Sc}$, but no GroEL (FIG. 5D). These effects of GroEL were dose-dependent (FIG. 5C).

5.2.2.3 GroEL Effects Require ATP, but not GroES

GroEL-promoted protein folding usually, but not always, requires the co-chaperone GroES and ATP (Hartl, 1996; Buchner, 1996). PrP conversion was not observed in the absence of ATP (FIG. 5E). Moreover, two point mutants of GroEL, which block release of substrate (D87K and 337/349; Kocisko et al., 1994) strongly reduced conversion (FIG. 5E). Surprisingly, however, the stimulating effects of GroEL on $^{35}S\text{-}PrP^{C}$ conversion were consistently eliminated by GroES (FIG. 5D). This inhibition was due to an effect of GroES on GroEL, rather than on PrP, because GroES did not inhibit the denaturant-promoted conversion of $^{35}S\text{-}PrP^{C}$ that occurs in the absence of GroEL.

5.2.2.4 Post-Translational PrP Modifications Modestly Affect Chaperone-Promoted Conversions The inventor used a PrP mutant that lacks the glycosylphosphatidylinositol (GPI) anchor ($PrP^{GPI-}$; Edenhofer et al., 1996; Freeman and Morimoto, 1996) and accumulates in mono- and unglycosylated form (FIG. 5F, right), to determine if these natural modifications affect chaperone-mediated conversion. Again, of the various chaperones tested, GroEL was the only one that efficiently stimulated conversion in the presence of untreated $PrP^{Sc}$ (FIG. 5F); and, once again, GroEL-promoted effects were ablated in the absence of ATP and inhibited by GroES (FIG. 5F). With this form of PrP, however, conversion was more efficient (typically 30-40%).

Moreover, conversion was also achieved with a combination of Hsp104, Hsp70, and Hsp40, albeit less consistently and less strongly than with GroEL (FIG. 5F). Results similar to those obtained with $PrP^{GPI-}$, were also obtained with unglycosylated $^{35}S\text{-}PrP^{C}$ purified from cells cultured with tunicamycin. Therefore, the ability of the chaperones to mediate the conversion of $^{35}S\text{-}PrP^{C}$ to PrP-res was modestly facilitated by the absence of N-linked sugars or the GPI-anchor.

5.2.2.5 Conversion Kinetics Reveal a Two-Step Process

When $^{35}S\text{-}PrP^{C}$ converts to PrP-res, it becomes associated with $PrP^{Sc}$, which is a pelletable aggregate (Caughey et al., 1995; Bessen et al., 1997). To gain insight into the chaperone-mediated conversion process, the inventor analyzed the kinetics of conversion, monitoring both protease-resistance and insolubility. GroEL promoted the acquisition of both of these signature features of $PrP^{Sc}$ in $^{35}S$-PrP (FIG. 6A and FIG. 6B). In reactions driven with untreated $PrP^{Sc}$ and GroEL, protease resistance was acquired at a pace similar to that observed in reactions nucleated with partially-denatured $PrP^{Sc}$, in the absence of GroEL (FIG. 6A). Moreover, in both sets of reactions, protease-resistant radioactivity was found only in pelletable material (FIG. 6C).

Surprisingly, however, when the rate at which $^{35}S$-PrP became insoluble was examined, the chaperone-driven reaction showed very different kinetics than those driven by partially-denatured PrP$^{Sc}$. No pelletable radioactivity was detected at two hours in reactions driven by partially-denatured PrP$^{Sc}$ (FIG. 6A and FIG. 6B). In striking contrast, in chaperone-driven reactions, the conversion of PrP to a pelletable form was virtually complete in two hours. This occurred long before $^{35}$S-PrP converted to its characteristic protease-resistant form (FIG. 6A and FIG. 6B). This pelleting of $^{35}$S-PrP$^C$ was almost certainly due to an association with pre-existing PrP$^{Sc}$, because in parallel reactions with GroEL, but without PrP$^{Sc}$, most $^{35}$S-PrP$^C$ remained soluble (FIG. 6B).

5.2.2.6 In reactions nucleated with partially-denatured PrP$^{Sc}$, Hsp104 Also Promotes Conversion Another chaperone was effective in reactions seeded with partially-denatured PrP$^{Sc}$. For these reactions, a milder denaturant, urea, was used because some chaperones are sensitive to inhibition by GdnHCl (Todd and Lorimor, 1995). Moreover, the lower basal rate of conversion obtained with urea (FIG. 7A, buffer) allowed the inventor to test the ability of other chaperones to either inhibit or stimulate conversion.

None inhibited (FIG. 7A). Several stimulated, but only to a small degree (FIG. 7A). Strikingly, under these conditions, in addition to GroEL, Hsp104 strongly stimulated conversion (FIG. 7A). With Hsp104, typically 20-30%, occasionally more than 50% of total $^{35}$S-PrP$^C$ converted. The stimulatory effects of Hsp104 required partial denaturation of PrP$^{Sc}$, with pre-treatments in 3-4 M urea being optimal (FIG. 7B).

5.2.2.7 Folded state of $PrP^{Sc}$ governs properties of chaperone-Promoted Conversion While some Hsp104 functions require ATP (Parsell and Lindquist, 1993; Schirmer et al., 1996), in these reactions nucleotide was somewhat stimulatory, but was not required (FIG. 7C). Furthermore, two ATPase-deficient Hsp104 mutants (KT218 and KT620; Pan et al., 1993) promoted $^{35}$S-$PrP^{C}$ conversion nearly as well as wild-type Hsp104 (FIG. 7C).

Remarkably, the use of partially-denatured $PrP^{Sc}$ changed the character of conversions promoted by GroEL as well. These conversions lost ATP-dependence (FIG. 7D). Moreover, they became refractory to GroES inhibition (FIG. 7A). Thus, chaperone-mediated conversions are mechanistically distinct in reactions nucleated with partially-denatured $PrP^{Sc}$, and those nucleated by untreated $PrP^{Sc}$.

5.2.2.8 Chemical Chaperones Inhibit Conversion

The inventor also tested the effects of several small organic molecules (or chemical chaperones) known to affect protein folding: sucrose, glycerol, trehalose, DMSO and the cyclodextrin compounds (Talzelt et al., 1996; Welch and Brown, 1996; Yancey et al., 1982). None of the compounds tested affected $^{35}$S-$PrP^{C}$ conversions in reactions without $PrP^{Sc}$, nor in reactions seeded with untreated $PrP^{Sc}$.

In reactions seeded with partially denatured $PrP^{Sc}$, DMSO had a complex dose-dependent effect, intermediate levels (1-3%) stimulated conversion 2-3 fold and higher levels (up to 30%) virtually eliminated conversion (FIG. 8). Glycerol (FIG. 8) and cyclodextrin compounds (α-, β-, γ-forms) had no effect. Sucrose and trehalose inhibited conversion. This inhibition was observed only at high concentrations, but is physiologically relevant because these osmolytes are known to accumulate to such levels in vivo under stressful conditions (Yancey et al., 1982).

5.2.3 Discussion

Recently, protein chaperones and small organic molecules have figured prominently among cellular factors speculated to influence conversion of $PrP^{C}$ to $PrP^{Sc}$ (Kenward et al., 1996; Talzelt et al., 1996; Telling et al., 1995; Edenhofer et al., 1996). In scrapie-infected cells, some of the same organic molecules the inventor tested have been shown to reduce the rate of $PrP^{Sc}$ formation (Talzelt et al., 1996). The inventor provides the first evidence that protein chaperones and small organic molecules can directly affect conformational transitions of PrP. The inventor's findings also provide the first direct demonstration that chaperone Hsp104 can alter the conformation state of another protein.

In studying the conversion of $PrP^{C}$ to PrP-res, the inventor employed previously characterized chaperones from bacteria and the eukaryotic cytosol because protein chaperones have not yet been identified in compartments where $PrP^{C}$ converts to $PrP^{Sc}$. Indeed, the site where conversion occurs is still unclear. WT $PrP^{C}$ is thought to convert extracellularly, within endosomes, or in caveolae (Caughey and Raymond, 1991; Borchelt et al., 1992; Vey et al., 1996). Mutant PrP, proposed to model inherited TSEs, can acquire certain $PrP^{Sc}$-like properties spontaneously in the ER/Golgi complex (Daude et al., 1997). Of the chaperones the inventor tested, only GroEL and Hsp104 affected conversion. The inventor's results indicate that such chaperone interactions in vivo are likely to be highly specific. Clearly, the elucidation of PrP chaperone interactions in vivo are of great import as they provide potential targets for therapeutic intervention.

The inventor's discoveries provide a unifying biochemical connection between mammalian TSEs (the so called "prion" diseases) and [PSI+], a novel genetic element in yeast (sometimes called a "yeast prion"; Wickner, 1994). The proposed "mammalian prion" determinant $PrP^{Sc}$, and the "yeast prion" determinant Sup35 are functionally unrelated and share no sequence identity. Moreso, [PSI+] produces a heritable change in metabolism rather than a lethal infection. However, both mammalian and yeast "prions" apparently share a common mode of transmission based upon self-propagating changes in protein conformation (Glover et al., 1997; Chernoff et al., 1995; Patino et al., 1996).

Among yeast chaperones, the striking specificity of Hsp104 for PrP conversions, and its known in vivo specificity in regulating [PSI+] (Wickner, 1994; Glover et al., 1997; Chernoff et al., 1995; Patino et al., 1996) suggest that conformations of PrP and Sup35 share an underlying biochemical similarity that allows for recognition by particular chaperones and prion-like conformational transitions. The present invention evidences the specific interactions of Hsp104 with PrP and Sup35 proteins using circular dichroism and ATP hydrolysis measurements.

The standard for testing the disease properties of PrP is to determine its protease resistance pattern. The protease resistant form is associated with disease. The inventor has shown that PrP when produced in yeast is protease resistant and that this protease resistant state depends upon the Hsp104 protein. Thus the protease-resistant character of PrP, which is the hallmark of its disease potential, is affected by manipulation of yeast cells. The inventor also shows that these same manipulations of yeast cells alter the folding state and protease resistance of a yeast amyloid protein. Together these results establish that manipulating yeast cells provides a general mechanism for studying factors that control the folding of amyloidogenic proteins. Amyloid proteins are important causative factors in many human diseases. Thus, the presently disclosed, inventive use of yeast cells provides an excellent system for testing and manipulating the folding state of amyloid proteins, which is useful in identifying therapeutic agents.

All of the methods and apparatus disclosed herein can be made and executed without undue experimentation in light of the present disclosure. While the compositions and methods of this invention have been described in terms of preferred embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

WO 96/39834, filed Jun. 6, 1996.
Baker et al., *Mol. Neurobiol.*, 8(1):25-39, 1994.
Bendheim et al., *Nature,* 310(5976):418-421, 1984.
Bertoni, Brown Goldfarb, Gajdusek, Omaha, "Familial Creutzfeldt-Jakob disease with the PRNP codon 200$^{-lys}$ mutation and supranuclear palsy but without myoclonus or periodic EEG complexes," *Neurology, Abstract,* 42(4, Suppl. 3):350, 1992.
Bessen, Kocisko, Raymond, Nandan, Lansbury, Caughey, *Nature,* 375:698-700, 1995.
Bessen, Raymond, Caughey, *J. Biol. Chem.,* 272:15227-15233, 1997.
Bockman et al., *N. Engl. J. Med.,* 312(2):73-78, 1985.
Bolton et al., *Arch. Biochem. Biophys.,* 258:1515-22, 1987.
Bolton et al., *Biochemistry* 23:5898-5905, 1984.
Bolton et al., *Science,* 218:1309-1311, 1982.
Borchelt, Taraboulos, Prusiner, *J. Biol. Chem.,* 267:16188-16199, 1992.
Bossers, Belt, Raymond, Caughey, de Vries, Smits, *Proc. Natl. Acad. Sci. USA,* 94:4931-4936, 1997.
Bruston, Weissman, Farr, Fenton, Horwich, *Nature,* 383:96-99, 1996.
Buchner, *FASEB J.,* 10:10-19, 1996.
Carlson, Goodman, Lovett, Taylor, Marshall, Peterson-Torchia, Westaway, Prusiner, *Mol. Cell. Biol.,* 8:5528-5540, 1988.
Caughey, Brown, Raymond, Katzenstein, Tresher, *J. Virol.,* 68:2135-2141, 1994.
Caughey, Chesebro, *Trends Cell Biol.,* 7:56-62, 1997.
Caughey, Dong, Bhat, Ernst, Hayes, Caughey, Biochemistry, 30:7672-7680, 1991.
Caughey, Raymond, Ernst, Race, *J. Virol.,* 65:6597-6603, 1991.
Caughey, Raymond, *J. Biol. Chem.,* 266:18217-18233, 1991.
Chernoff, Lindquist, Ono, Inge-Vechtomov, Liebman, "Role of the chaperone protein Hep104 in propagation of the yeast prion-like factor [psi-F]," *Science,* 268:880-884, 1995.
Cyr, Lu, Douglas, *J. Biol. Chem.,* 267:20927-20931, 1992.
DebBurman, Raymond, Caughey, Lindquist, "Chaperone-supervised conversion of prion protein to its protease-resistant form," *Proc. Natl. Acad. Sci. USA,* 94:13938-13943, 1997.
Dlouhy, Hsiao, Farlow et al., "Linkage of the Indiana kindred of Gerstmann-Sträussler-Scheinker disease to the prion protein gene," *Nat. Genet.,* 1:64-67, 1992.
Doh-ura, Tateishi, Sasaki, Kitamoto, Sakaki, "Pro-Leu change at position 102 of prion protein is the most common but not the sole mutation related to Gerstmann-Sträussler syndrome," *Biochem. Biophys. Res. Commun.,* 1163:974-979, 1989.
Edenhofer, Reiger, Famulok, Weiss, Winnacker, *J. Virol.,* 70:4724-4728, 1996.
Freeman, Morimoto, *EMBO J.,* 15:2969-2979, 1996.
Gabizon, Rosenmann, Meiner et al., "Mutation and polymorphism of the prion protein gene in Libyan Jews with Creutzfeldt-Jakob disease," *Am. J. Hum. Genet.,* 33:828-835, 1993.
Gasset, Baldwin, Lloyd, Gabriel, Holtzman, Cohen, Fletterick, Prusiner, *Proc. Natl. Acad. Sci. USA,* 89:10940-10944, 1992.
Glover, Kowal, Schirmer, Patino, Liu, Lindquist, "Self-seeded fibers formed by Sup35, the protein determinant of [PSI+], a heritable prion-like factor of *Saccharomyces cerevisiae,*" *Cell,* 89:811-819, 1997.
Goldfarb, Brown, Vrbovská et al., "An insert mutation in the chromosome 20 amyloid precursor gene in a Gerstmann-Sträussler-Scheinker family," *J. Nurol. Sci.,* 111:189-194, 1992.
Goldfarb, Haltia, Brown et al., "New mutation in scrapie amyloid precursor gene (at codon 178) in Finnish Creutzfeldt-Jakob kindred," *Lancet,* 337:425, 1991.
Goldfarb, Korczyn, Brown, Chapman, Gajdusek, "Mutation in codon 200 of scrapie amyloid precursor gene linked to Creutzfeldt-Jakob disease in Sephardic Jews of Libyan and non-Libyan origin," *Lancet,* 336:637-638, 1990.
Goldgaber, Goldfarb, Brown et al., "Mutations in familial Crutzfeldt-Jakob disease and Gerstmann-Sträussler-Scheinker's syndrome," *Exp. Neurol.,* 106:204-206, 1989.
Griffith, *Nature,* 215:1043-1044, 1967.
Guiroy et al., *Neurosci Lett,* 155(1):112-115, 1993.
Hartl, *Nature,* 381:571-580, 1996.
Hsiao, Baker, Crow et al., "Linkage of a prion protein misense variant to Gerstmann-Sträussler syndrome," *Nature,* 338:342-345, 1989.
Hwang, Woo, Goldberg, Chung, *J. Biol. Chem.,* 263:8727-8734, 1988.
Kenward, Landon, Laszlo, Mayor, *Cell Stress & Chaperones,* 1:18-22, 1996.
King, Tittmann, Gross, Gebert, Aebi, Wuthrich, *Proc. Natl. Acad. Sci. USA,* 94:6618-6622, 1997.
Kitamoto, Iizuka, Tateishi, "An amber mutation of prion protein in Gerstmann-Sträussler syndrome with mutant PrP plaques," *Biochem. Biophys. Res. Commun.,* 192:525-531, 1993a.
Kitamoto, Ohta, Doh-ura, Hitoshi, Terao, Tateishi, "Novel missense variants of prion protein in Creutzfeldt-Jakob disease or Gerstmann-Sträussler syndrome," *Biochem. Biophys. Res. Commun.,* 191:709-714, 1993b.
Klunk, Pettegrew, Abraham, *J. Histochem. Cytochem.,* 37:1273-1279, 1989.
Kocisko, Come, Priola, Chesebro, Raymond, Lansbury, Caughey, *Nature,* 370:471-474, 1994.
Kocisko, Priola, Raymond, Chesebro, Lansbury, Lansbury, *Proc. Natl. Acad. Sci. USA,* 92:3923-3927, 1995.
Lansbury and Caughey Chem. Biol 2:1-5, 1995
Lanzetta, Alvarez, Reinach, Candia, *Analyt. Biochem.,* 100:95-97, 1979.
Lee, Pokala, *J. Biol. Chem.,* 270:10432-10438, 1995.
Lehmann and Harris, J. Biol. Chem. 271:1633-1637, 1997.
Lindquist, *Cell,* 89:495-498, 1997.
Masters, Harris, Gajdusek, Gibbs, Bernouilli, Asher, Creutzfeldt-Jakob disease: patterns of worldwide occurrence and the significance of familial and sporadic clustering," *Ann. Neurol.,* 5:177-188, 1978.

Maurizi, Thompson, Singh, Kim, *Meth. in Enzymol.*, 244: 314-331, 1994.

McKinley et al., *Cells*, 35:57-62, 1982.

Medori, Tritschler, LeBlanc et al., "Fatal familial insomnia, a prion disease with a mutation at codon 178 of the prion protein gene," *N. Engl. J. Med.*, 326:444-449, 1992.

Mehlhorn et al., *Biochemistry*, 35:5528-5537, 1996.

Mendosa, Rogers, Lorimer, Horowitz, *J. Biol. Chem.*, 266: 13044, 1991.

Muller-Hill and Beyreuther, *Ann. Rev. Biochem.*, 38:287-307, 1989.

Nakamura et al. Biochem. Biophys. Res. Comm.

Nguyen, Baldwin, Cohen, Prusiner, *Biochemistry*, 34:4186-4192, 1995.

Oesch et al., *Cell*, 40:735-746, 1985.

Pan, Baldwin, Nguyen, Gasset, Serban, Groth, Mehlhorn, Huang, Fletterick, Cohen, Prusiner, *Proc. Natl. Acad. Sci. USA*, 90:10962-10966, 1993.

Parsell, Kowal, Lindquist, *J. Biol. Chem.*, 269:4480-4487, 1994.

Parsell, Kowal, Singer, Lindquist, "Protein disaggregation mediated by heat-shock protein HSPI04," *Nature*, 372: 475-478, 1994.

Parsell, Kowal, Singer, Lindquist, *Nature*, 353:270-272, 1991.

Parsell, Lindquist, *Ann. Rev. Genet.*, 27:437-496, 1993.

Patino, Liu, Glover, Lindquist, "Support for the prion hypothesis for inheritance of a phenotypic trait in yeast," *Science*, 273:622-626, 1996.

Paushkin, Kushnirov, Smirnov, Ter-Avanesyan, *EMBO J.*, 15:3127-3134, 1996.

Paushkin, Kushnirov, Smirnov, Ter-Avanesyan, *Science*, 277: 381-383, 1997.

Petersen, Tabaton, Berg et al., "Analysis of the prion protein gene in thalamic dementia," *Neurology*, 42:1859-1863, 1992.

Pike et al., *J. Neurosci.* 13:1676-1687, 1993.

Poulter, Baker, Frith et al., "Inherited prion disease with 144 base pair gene insertion. 1. Genealogical and molecular studies," *Brain*, 115:675-685, 1992.

Prusiner et al., *Cell*, 38:127-134, 1984.

Prusiner, Bolton, Groth, Bowman, Cochran, McKinley, *Biochemistry*, 21:6942-6950, 1982.

Prusiner, in Fields Virology (eds. Fields, B. N., Knipe, D. M. & Howley, P. M.) 2901-2950 (Lippencott-Raven Publishers, Philadelphia), 1996.

Prusiner, McKinley, Bowman et. al., *Cell*, 35:349-358, 1983.

Prusiner, *Trends Biochem. Sci.*, 21:482-487, 1996.

Raymond, Hope, Kocisko, Priola, Raymond, Bossers, Ironside, Will, Chen, Peterson, Gambetti, Rubenstein, Smits, Lansbury, Caughey, *Nature*, 388:285-288, 1997.

Riek, Hornemann, Wider, Billeter, Glockshuber, Wuthrich, *Nature*, 382:180-184, 1996.

Sanchez, Lindquist, *Science*, 248:1112-1115, 1990.

Schirmer and Lindquist, "Interactions of the chaperone Hsp104 with yeast Sup35 and mammalian PrP," *Proc. Natl. Acad. Sci. USA*, 94:13932-13937, 1997.

Schirmer, Glover, Singer, Lindquist, *Trends Biochem. Sci.*, 21:289-296, 1996.

Talzelt, Prusiner, Welch, *EMBO J.*, 15: 6363-6373, 1996.

Tashima et al., *Brain Res.*, 399(1):80-86, 1986.

Telling, Scott, Mastrianni, Gabizon, Torchia, Cohen, DeArmond, Prusiner, *Cell*, 83:79-90, 1995.

Ter-Avanesyan, Kushnirov, Dagkesamanskaya, Didichenko, Chernoff, Inge-Vechtomov, Smirnov, *Mol. Microb.*, 7:683-692, 1993.

Todd, Lorimer, *J. Biol. Chem.*, 270:5388-5394, 1995.

Vey, Pilkuhn, Wille, Nixon, DeArmond, Smart, Anderson, Taraboulos, Prusiner, *Proc. Natl. Acad. Sci. USA*, 93:14945-14949, 1996.

Wawrzynow, Wojtkowiak, Marszalek, Banecki, Jonsen, Graves, Georgopoulos, Zylicz, *EMBO-J.*, 14:1867-1877, 1995.

Welch, Brown, *Cell Stress & Chaperones*, 1:109-115, 1996.

Wickner, Gottesman, Skowyra, Hoskins, McKenney, Maurizi, Proc. Natl. Acad. Sci. USA, 91:12218-12222, 1994.

Wickner, *Science*, 264:566-569, 1994.

Wu, Chen, *Analyt. Biochem.*, 177:178-182, 1989.

Yancey, Clark, Hand, Bowlus, Somero, *Science*, 217:1214-1222, 1982.

Zeigelhoffer, Lopez-Buesa, Craig, *J. Biol. Chem.*, 270: 10412-10419, 1995.

Zhang, Kaneko, Nguyen, Livshits, Baldwin, Cohen, James, Prusiner, *J. Molec. Biol.*, 250:514-526, 1995.

Zhang, Stockel, Mehlhorn, Groth, Baldwin, Prusiner, James, Cohen, *Biochemistry*, 36:3543-3553, 1997.

What is claimed is:

1. A method of identifying a candidate substance that inhibits the aggregation of a mammalian aggregate-prone amyloid protein in a yeast cell, comprising:
    (a) contacting a yeast cell that expresses a chimeric protein comprising a mammalian aggregate-prone amyloid protein with said candidate substance under conditions effective to allow aggregated amyloid formation in the yeast cell, wherein the chimeric protein comprises at least an aggregate forming domain of β-amyloid; and
    (b) determining the ability of said candidate substance to inhibit the aggregation of the aggregate-prone amyloid protein in the yeast cell.

2. The method of claim 1, wherein the chimeric protein comprises at least an aggregate forming domain of a mammalian aggregate-prone amyloid protein operably attached to a detectable marker protein.

3. The method of claim 2, wherein said marker protein is green fluorescent protein or luciferase.

4. The method of claim 2, wherein said marker protein is a drug-resistance marker protein.

5. The method of claim 2, wherein said marker protein is a hormone receptor.

6. The method of claim 5, wherein said hormone receptor is a glucocorticoid receptor.

7. The method of claim 1, wherein the chimeric protein comprises at least amino acids 1-42 of β-amyloid.

8. The method of claim 1, wherein the chimeric protein comprises Sup35 in which the N-terminal domain has been replaced by amino acids 1-42 of β-amyloid.

9. The method of claim 1, wherein any aggregation of the mammalian aggregate-prone amyloid protein is detected by the ability of the aggregated protein to bind Congo Red.

10. The method of claim 1, wherein any aggregation of the mammalian aggregate-prone amyloid protein is detected by increased protease resistance of the aggregated protein.

11. The method of claim 1, wherein the aggregate-prone amyloid protein is labeled.

12. The method of claim 11, wherein the label is a radioactive isotope, a fluorophore, or a chromophore.

13. The method of claim 12, wherein the label is $^{35}$S.

14. The method of claim 12, wherein the fluorophore comprises a green fluorescent protein polypeptide.

15. The method of claim 1, wherein said yeast cell overexpresses Hsp104.

16. The method of claim 1, wherein aggregated amyloid formation is evidenced by the formation of fibrillary material.

17. A method of identifying a candidate substance that inhibits the aggregation of a mammalian aggregate-prone amyloid protein in a yeast cell, comprising:
- (a) contacting a yeast cell that expresses a chimeric protein comprising a mammalian aggregate-prone amyloid protein with said candidate substance under conditions effective to allow aggregated amyloid formation in the yeast cell, wherein the chimeric protein comprises at least an aggregate forming domain of prion protein; and
- (b) determining the ability of said candidate substance to inhibit the aggregation of the aggregate-prone amyloid protein in the yeast cell.

18. The method of claim 17, wherein the chimeric protein comprises at least an aggregate forming domain of a mammalian aggregate-prone amyloid protein operably attached to a detectable marker protein.

19. The method of claim 18, wherein said marker protein is green fluorescent protein or luciferase.

20. The method of claim 18, wherein said marker protein is a drug-resistance marker protein.

21. The method of claim 18, wherein said marker protein is a hormone receptor.

22. The method of claim 21, wherein said hormone receptor is a glucocorticoid receptor.

23. The method of claim 17, wherein any aggregation of the mammalian aggregate-prone amyloid protein is detected by the ability of the aggregated protein to bind Congo Red.

24. The method of claim 17, wherein any aggregation of the mammalian aggregate-prone amyloid protein is detected by increased protease resistance of the aggregated protein.

25. The method of claim 17, wherein the aggregate-prone amyloid protein is labeled.

26. The method of claim 25, wherein the label is a radioactive isotope, a fluorophore, or a chromophore.

27. The method of claim 26, wherein the label is $^{35}$S.

28. The method of claim 26, wherein the fluorophore comprises a green fluorescent protein polypeptide.

29. The method of claim 17, wherein said yeast cell overexpresses Hsp104.

30. The method of claim 17, wherein aggregated amyloid formation is evidenced by the formation of fibrillary material.

* * * * *

UNITED STATES PATENT AND TRADEMARK OFFICE
CERTIFICATE OF CORRECTION

| | | |
|---|---|---|
| PATENT NO. | : 7,799,535 B1 | |
| APPLICATION NO. | : 09/207649 | |
| DATED | : September 21, 2010 | |
| INVENTOR(S) | : Susan Lindquist | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 159 days.

Signed and Sealed this
Twelfth Day of July, 2011

David J. Kappos
*Director of the United States Patent and Trademark Office*